United States Patent
Bloom et al.

(10) Patent No.: US 10,314,647 B2
(45) Date of Patent: *Jun. 11, 2019

(54) ELECTROSURGICAL CUTTING INSTRUMENT

(71) Applicant: MEDTRONIC ADVANCED ENERGY LLC, Minneapolis, MN (US)

(72) Inventors: Eliot F. Bloom, Hopkinton, NH (US); Phillip Berman, Jacksonville, FL (US); Wenjeng Li, Saint Johns, FL (US); David J. Little, Ponte Vedra, FL (US); Dana A. Oliver, Jacksonville, FL (US); John R. Prisco, Jacksonville, FL (US); Phillip P. Brown, Jacksonville, FL (US); Patrick Richart, Jacksonville, FL (US)

(73) Assignee: Medtronic Advanced Energy LLC, Minneapolis, MN (US)

( * ) Notice: Subject to any disclaimer, the term of this patent is extended or adjusted under 35 U.S.C. 154(b) by 880 days.

This patent is subject to a terminal disclaimer.

(21) Appl. No.: 14/579,579

(22) Filed: Dec. 22, 2014

(65) Prior Publication Data
US 2015/0173827 A1 Jun. 25, 2015

Related U.S. Application Data

(60) Provisional application No. 61/920,412, filed on Dec. 23, 2013, provisional application No. 61/933,521, filed on Jan. 30, 2014.

(51) Int. Cl.
*A61B 18/14* (2006.01)
*A61B 18/00* (2006.01)
*A61B 18/12* (2006.01)

(52) U.S. Cl.
CPC .. *A61B 18/148* (2013.01); *A61B 2018/00148* (2013.01); *A61B 2018/00202* (2013.01);
(Continued)

(58) Field of Classification Search
CPC ........ A61B 18/148; A61B 2018/00148; A61B 2018/00202; A61B 2018/00208;
(Continued)

(56) References Cited

U.S. PATENT DOCUMENTS

| | | |
|---|---|---|
| 2,888,928 A | 6/1959 | Seiger |
| 3,682,130 A | 8/1972 | Jeffers |

(Continued)

FOREIGN PATENT DOCUMENTS

| | | |
|---|---|---|
| WO | WO/98/34550 | 8/1998 |
| WO | WO/03/079911 | 10/2003 |

OTHER PUBLICATIONS

MicroPenning: How It Works: MicroPen Technologies, http://www.micropen.com/Micropenning/how_it_works.php, Exhibit in Case IPR2016-01405, Sep. 13, 2010, 3 pgs.

(Continued)

*Primary Examiner* — Jaymi E Della
(74) *Attorney, Agent, or Firm* — Dicke, Billig & Czaja, PLLC

(57) ABSTRACT

An electrosurgical device having a tubular outer shaft and an inner shaft is disclosed. The tubular outer shaft includes an axis and a distal end region. The distal end region includes a distal-most tip and a cutting edge defining a window in the outer shaft proximal along the axis to the distal-most tip. The inner shaft inner shaft coaxially maintained within the outer shaft such that the inner shaft is movable about the axis with respect to the outer shaft and wherein a portion of the inner shaft is exposed in the window of the outer shaft. A first electrode is disposed on the outer shaft in a region proximal (Continued)

along the axis to the window, and a second electrode is electrically isolated from the first electrode and disposed on the inner shaft. The second electrode is exposed in the window of the outer shaft.

19 Claims, 13 Drawing Sheets

(52) U.S. Cl.
CPC .............. *A61B 2018/00208* (2013.01); *A61B 2018/00565* (2013.01); *A61B 2018/00601* (2013.01); *A61B 2018/126* (2013.01); *A61B 2218/002* (2013.01); *A61B 2218/007* (2013.01)

(58) Field of Classification Search
CPC ........... A61B 2018/00565; A61B 2018/00601; A61B 2018/126; A61B 2218/002; A61B 2218/007; A61B 2018/00595; A61B 2018/00607; A61B 2018/0063; A61B 18/1402; A61B 18/1445; A61B 18/14; A61B 18/04
USPC ........................................................ 606/50
See application file for complete search history.

(56) References Cited

U.S. PATENT DOCUMENTS

| | | |
|---|---|---|
| 3,750,650 A | 8/1973 | Ruttgers |
| 4,060,088 A | 11/1977 | Morrison, Jr. et al. |
| 4,195,637 A | 4/1980 | Gruntzig et al. |
| 4,207,897 A | 6/1980 | Lloyd et al. |
| 4,248,224 A | 2/1981 | Jones |
| 4,932,952 A | 6/1990 | Wojciechowicz, Jr. |
| 4,943,290 A | 7/1990 | Rexroth et al. |
| 4,950,232 A | 8/1990 | Ruzicka et al. |
| 4,985,030 A | 1/1991 | Melzer et al. |
| 4,998,933 A | 3/1991 | Eggers et al. |
| 5,190,541 A | 3/1993 | Abele et al. |
| 5,195,959 A | 3/1993 | Smith |
| 5,234,428 A | 8/1993 | Kaufman |
| 5,254,117 A | 10/1993 | Rigby et al. |
| 5,281,215 A | 1/1994 | Midler |
| 5,330,521 A | 7/1994 | Cohen |
| 5,334,181 A | 8/1994 | Rubinsky et al. |
| 5,336,220 A | 8/1994 | Ryan et al. |
| 5,364,395 A | 11/1994 | West |
| 5,383,874 A | 1/1995 | Jackson et al. |
| 5,385,148 A | 1/1995 | Lesh et al. |
| 5,395,312 A | 3/1995 | Desai |
| 5,401,272 A | 3/1995 | Perkins |
| 5,405,376 A | 4/1995 | Mulier et al. |
| 5,417,709 A | 5/1995 | Slater |
| 5,431,168 A | 7/1995 | Webster, Jr. |
| 5,431,649 A | 7/1995 | Mulier et al. |
| 5,441,503 A | 8/1995 | Considine et al. |
| 5,443,463 A | 8/1995 | Stern et al. |
| 5,445,638 A | 8/1995 | Rydell et al. |
| 5,460,629 A | 10/1995 | Shlain et al. |
| 5,490,819 A | 2/1996 | Nicholas et al. |
| 5,492,527 A | 2/1996 | Glowa et al. |
| 5,496,271 A | 3/1996 | Burton et al. |
| 5,505,700 A | 4/1996 | Leone |
| 5,521,576 A | 5/1996 | Collins |
| 5,540,562 A | 7/1996 | Giter |
| 5,542,196 A | 8/1996 | Hirsch et al. |
| 5,542,945 A | 8/1996 | Fritzsch |
| 5,556,397 A | 9/1996 | Long et al. |
| 5,562,702 A | 10/1996 | Huitema et al. |
| 5,569,243 A | 10/1996 | Kortenbach et al. |
| 5,573,424 A | 11/1996 | Poppe |
| 5,595,183 A | 1/1997 | Swanson et al. |
| 5,599,346 A | 2/1997 | Edwards et al. |
| 5,605,539 A | 2/1997 | Buelna et al. |
| 5,647,869 A | 7/1997 | Goble et al. |
| 5,685,838 A | 11/1997 | Peters et al. |
| 5,688,267 A | 11/1997 | Panescu et al. |
| 5,697,536 A | 12/1997 | Eggers et al. |
| 5,713,942 A | 2/1998 | Stern |
| 5,733,280 A | 3/1998 | Avitall |
| 5,743,903 A | 4/1998 | Stern et al. |
| 5,766,167 A | 6/1998 | Eggers et al. |
| 5,797,905 A | 8/1998 | Fleischman et al. |
| 5,797,960 A | 8/1998 | Stevens et al. |
| 5,810,764 A | 9/1998 | Eggers et al. |
| 5,810,802 A | 9/1998 | Panescu et al. |
| 5,827,216 A | 10/1998 | Igo et al. |
| 5,836,947 A | 11/1998 | Fleischman et al. |
| 5,840,030 A | 11/1998 | Ferek-Petric et al. |
| 5,843,021 A | 12/1998 | Edwards et al. |
| 5,843,152 A | 12/1998 | Tu et al. |
| 5,873,855 A | 2/1999 | Eggers et al. |
| 5,891,142 A | 4/1999 | Eggers et al. |
| 5,895,355 A | 4/1999 | Schaer |
| 5,897,553 A | 4/1999 | Mulier |
| 5,904,681 A | 5/1999 | West, Jr. |
| 5,913,854 A | 6/1999 | Maguire et al. |
| 5,916,213 A | 6/1999 | Haissaguerre et al. |
| 5,921,982 A | 7/1999 | Lesh et al. |
| 5,925,045 A | 7/1999 | Reimels et al. |
| 5,927,284 A | 7/1999 | Borst et al. |
| 5,935,123 A | 8/1999 | Edwards et al. |
| 5,944,715 A | 8/1999 | Goble et al. |
| 5,928,191 A | 9/1999 | Houser et al. |
| 5,971,980 A | 10/1999 | Sherman |
| 5,971,983 A | 10/1999 | Lesh |
| 5,975,919 A | 11/1999 | Arnett et al. |
| 5,980,516 A | 11/1999 | Mulier et al. |
| 5,989,248 A | 11/1999 | Tu et al. |
| 5,991,650 A * | 11/1999 | Swanson .............. A61B 5/0422 374/E1.005 |
| 5,993,412 A | 11/1999 | Deily et al. |
| 6,004,316 A | 12/1999 | Laufer |
| 6,004,319 A | 12/1999 | Goble et al. |
| 6,010,500 A | 1/2000 | Sherman et al. |
| 6,012,457 A | 1/2000 | Lesh |
| 6,015,391 A | 1/2000 | Rishton et al. |
| 6,024,733 A | 2/2000 | Eggers et al. |
| 6,042,556 A | 3/2000 | Beach et al. |
| 6,063,081 A | 5/2000 | Mulier |
| 6,071,279 A | 6/2000 | Whayne et al. |
| 6,088,894 A | 7/2000 | Oakley |
| 6,096,037 A | 8/2000 | Mulier |
| 6,117,101 A | 9/2000 | Diederich et al. |
| 6,142,993 A | 11/2000 | Whayne et al. |
| 6,142,994 A | 11/2000 | Swanson et al. |
| 6,152,920 A | 11/2000 | Thompson et al. |
| 6,161,543 A | 12/2000 | Cox et al. |
| 6,165,174 A | 12/2000 | Jacobs et al. |
| 6,193,715 B1 | 2/2001 | Wrublewski |
| 6,217,528 B1 | 4/2001 | Koblish et al. |
| 6,217,576 B1 | 4/2001 | Tu et al. |
| 6,221,088 B1 * | 4/2001 | Bays ................ A61B 17/32002 604/22 |
| 6,224,592 B1 | 5/2001 | Eggers et al. |
| 6,231,518 B1 | 5/2001 | Grabek et al. |
| 6,235,024 B1 | 5/2001 | Tu |
| 6,237,605 B1 | 5/2001 | Vaska et al. |
| 6,238,347 B1 | 5/2001 | Nix et al. |
| 6,238,393 B1 | 5/2001 | Mulier |
| 6,245,061 B1 | 6/2001 | Panescu et al. |
| 6,245,064 B1 | 6/2001 | Lesh et al. |
| 6,245,065 B1 | 6/2001 | Panescu et al. |
| 6,251,092 B1 | 6/2001 | Qin et al. |
| 6,251,128 B1 | 6/2001 | Knopp et al. |
| 6,270,471 B1 | 8/2001 | Hechel et al. |
| 6,293,943 B1 | 9/2001 | Panescu et al. |
| 6,293,952 B1 | 9/2001 | Peters et al. |
| 6,293,957 B1 | 9/2001 | Peters et al. |
| 6,325,797 B1 | 12/2001 | Stewart et al. |
| 6,328,736 B1 | 12/2001 | Mulier |
| 6,332,881 B1 | 12/2001 | Carner et al. |
| 6,358,248 B1 | 3/2002 | Mulier |

(56) References Cited

U.S. PATENT DOCUMENTS

| | | |
|---|---|---|
| 6,361,531 B1 | 3/2002 | Hissong |
| 6,364,876 B1 | 4/2002 | Erb et al. |
| 6,368,275 B1 | 4/2002 | Sliwa et al. |
| 6,383,151 B1 | 5/2002 | Diederich et al. |
| 6,385,472 B1 | 5/2002 | Hall et al. |
| 6,398,792 B1 | 6/2002 | O'Connor |
| 6,409,722 B1 | 6/2002 | Hoey |
| 6,413,254 B1 | 7/2002 | Hissong et al. |
| 6,419,648 B1 | 7/2002 | Vitek et al. |
| 6,425,867 B1 | 7/2002 | Vaezy et al. |
| 6,430,426 B2 | 8/2002 | Avitall |
| 6,440,130 B1 | 8/2002 | Mulier |
| 6,443,952 B1 | 9/2002 | Mulier |
| 6,461,357 B1 | 10/2002 | Sharkey et al. |
| 6,468,272 B1 * | 10/2002 | Koblish ............ A61B 18/1482 600/374 |
| 6,471,697 B1 | 10/2002 | Lesh |
| 6,471,698 B1 | 10/2002 | Edwards et al. |
| 6,474,340 B1 | 11/2002 | Vaska et al. |
| 6,475,216 B2 | 11/2002 | Mulier |
| 6,477,396 B1 | 11/2002 | Mest et al. |
| 6,484,727 B1 | 11/2002 | Vaska et al. |
| 6,488,678 B2 | 12/2002 | Sherman |
| 6,488,680 B1 | 12/2002 | Francischelli |
| 6,502,575 B1 | 1/2003 | Jacobs et al. |
| 6,503,263 B2 | 1/2003 | Adams |
| 6,514,250 B1 | 2/2003 | Jahns |
| 6,527,767 B2 | 3/2003 | Wang et al. |
| 6,537,248 B2 | 3/2003 | Mulier |
| 6,537,272 B2 | 3/2003 | Hoey |
| 6,558,382 B2 | 5/2003 | Jahns |
| 6,558,385 B1 | 5/2003 | Bloom et al. |
| 6,565,561 B1 | 5/2003 | Goble et al. |
| 6,584,360 B2 | 6/2003 | Francischelli |
| 6,585,732 B2 | 7/2003 | Mulier |
| 6,605,084 B2 | 8/2003 | Acker et al. |
| 6,610,055 B1 | 8/2003 | Swanson et al. |
| 6,610,060 B2 | 8/2003 | Mulier |
| 6,613,048 B2 | 9/2003 | Mulier |
| 6,645,199 B1 | 11/2003 | Jenkins et al. |
| 6,648,883 B2 | 11/2003 | Francischelli |
| 6,656,175 B2 | 12/2003 | Francischelli |
| 6,663,627 B2 | 12/2003 | Francischelli |
| 6,663,628 B2 | 12/2003 | Peters |
| 6,689,131 B2 | 2/2004 | McClurken |
| 6,699,240 B2 | 3/2004 | Francischelli |
| 6,702,810 B2 | 3/2004 | McClurken et al. |
| 6,702,811 B2 | 3/2004 | Stewart et al. |
| 6,706,038 B2 | 3/2004 | Francischelli |
| 6,706,039 B2 | 3/2004 | Mulier |
| 6,716,211 B2 | 4/2004 | Mulier |
| 6,736,810 B2 | 5/2004 | Hoey |
| 6,755,827 B2 | 6/2004 | Mulier |
| 6,764,487 B2 | 7/2004 | Mulier |
| 6,773,433 B2 | 8/2004 | Stewart et al. |
| 6,776,780 B2 | 8/2004 | Mulier |
| 6,780,180 B1 | 8/2004 | Goble et al. |
| 6,807,968 B2 | 10/2004 | Francischelli |
| 6,827,715 B2 | 12/2004 | Francischelli |
| 6,849,073 B2 | 2/2005 | Hoey |
| 6,858,028 B2 | 2/2005 | Mulier |
| 6,887,238 B2 | 5/2005 | Jahns |
| 6,899,711 B2 | 5/2005 | Stewart et al. |
| 6,911,019 B2 | 6/2005 | Mulier |
| 6,916,318 B2 | 7/2005 | Francischelli |
| 6,936,046 B2 | 8/2005 | Hissong |
| 6,949,097 B2 | 9/2005 | Stewart et al. |
| 6,949,098 B2 | 9/2005 | Mulier |
| 6,953,461 B2 | 10/2005 | Bloom et al. |
| 6,960,205 B2 | 11/2005 | Jahns |
| 6,962,589 B2 | 11/2005 | Mulier |
| 6,979,332 B2 | 12/2005 | Adams |
| 7,052,494 B2 * | 5/2006 | Goble ............ A61B 17/32002 606/45 |
| 7,150,747 B1 * | 12/2006 | McDonald ............ A61B 18/148 606/180 |
| 7,166,103 B2 | 1/2007 | Carmel et al. |
| 7,229,437 B2 * | 6/2007 | Johnson ............ A61B 5/0422 606/27 |
| 7,232,439 B2 * | 6/2007 | Ciarrocca ............ A61B 18/148 606/180 |
| 7,232,440 B2 | 6/2007 | Dumbauld et al. |
| 7,247,155 B2 | 7/2007 | Hoey et al. |
| 7,261,711 B2 | 8/2007 | Mulier et al. |
| 7,278,994 B2 | 10/2007 | Goble |
| 7,309,325 B2 | 12/2007 | Mulier et al. |
| 7,311,708 B2 | 12/2007 | McClurken |
| 7,322,974 B2 | 1/2008 | Swoyer et al. |
| 7,361,175 B2 | 4/2008 | Suslov |
| 7,364,579 B2 | 4/2008 | Mulier et al. |
| 7,537,595 B2 | 5/2009 | McClurken |
| 7,604,635 B2 | 10/2009 | Bloom et al. |
| 7,608,072 B2 | 10/2009 | Swanson |
| 7,645,277 B2 | 1/2010 | Bloom et al. |
| 7,651,494 B2 | 1/2010 | Bloom et al. |
| 7,674,263 B2 | 3/2010 | Ryan |
| 7,691,050 B2 | 4/2010 | Gellman |
| 7,736,361 B2 | 6/2010 | Palanker |
| 7,785,337 B2 | 8/2010 | Adams et al. |
| 7,811,282 B2 | 10/2010 | McClurken |
| 7,815,634 B2 | 10/2010 | Bloom et al. |
| 7,854,736 B2 | 12/2010 | Ryan |
| 7,909,820 B2 | 3/2011 | Lipson |
| 7,942,872 B2 | 5/2011 | Ein-Gal |
| 7,976,544 B2 | 7/2011 | McClurken |
| 7,993,337 B2 | 8/2011 | Lesh |
| 7,997,278 B2 | 8/2011 | Utley et al. |
| 7,998,140 B2 | 8/2011 | McClurken |
| 8,012,153 B2 | 9/2011 | Woloszko et al. |
| 8,034,071 B2 | 10/2011 | Scribner et al. |
| 8,038,670 B2 | 10/2011 | McClurken |
| 8,048,070 B2 | 11/2011 | O'Brien |
| 8,083,736 B2 | 12/2011 | Bloom et al. |
| 8,105,323 B2 | 1/2012 | Buysse et al. |
| 8,172,828 B2 | 4/2012 | Chang et al. |
| 8,177,783 B2 | 5/2012 | Davison et al. |
| 8,216,233 B2 | 7/2012 | McClurken |
| 8,317,786 B2 | 11/2012 | Dahla et al. |
| 8,323,276 B2 | 12/2012 | Palanker et al. |
| 8,348,946 B2 | 1/2013 | McClurken |
| 8,361,068 B2 | 1/2013 | McClurken |
| 8,377,086 B2 | 2/2013 | Flynn et al. |
| 8,388,642 B2 | 3/2013 | Muni et al. |
| 8,414,572 B2 | 4/2013 | Davison et al. |
| 8,688,237 B2 | 4/2014 | Stanislaus et al. |
| 9,289,141 B2 | 3/2016 | Lowery et al. |
| 2001/0007938 A1 | 7/2001 | Long |
| 2002/0049483 A1 | 4/2002 | Knowlton |
| 2002/0062131 A1 | 5/2002 | Gallo, Sr. |
| 2002/0082643 A1 | 6/2002 | Kammerer et al. |
| 2003/0014050 A1 | 1/2003 | Sharkey et al. |
| 2003/0032954 A1 | 2/2003 | Carranza et al. |
| 2003/0045872 A1 | 3/2003 | Jacobs |
| 2003/0073993 A1 | 4/2003 | Ciarrocca |
| 2003/0144656 A1 | 7/2003 | Ocel |
| 2003/0191462 A1 | 10/2003 | Jacobs |
| 2003/0204185 A1 | 10/2003 | Sherman et al. |
| 2003/0216724 A1 | 11/2003 | Jahns |
| 2004/0015106 A1 | 1/2004 | Coleman |
| 2004/0015219 A1 | 1/2004 | Francischelli |
| 2004/0024395 A1 | 2/2004 | Ellman et al. |
| 2004/0044340 A1 | 3/2004 | Francischelli |
| 2004/0049179 A1 | 3/2004 | Francischelli |
| 2004/0078069 A1 | 4/2004 | Francischelli |
| 2004/0082948 A1 | 4/2004 | Stewart et al. |
| 2004/0087940 A1 | 5/2004 | Jahns |
| 2004/0092926 A1 | 5/2004 | Hoey |
| 2004/0111136 A1 | 6/2004 | Sharkey et al. |
| 2004/0111137 A1 | 6/2004 | Sharkey et al. |
| 2004/0116923 A1 | 6/2004 | Desinger |
| 2004/0138621 A1 | 7/2004 | Jahns |
| 2004/0138656 A1 | 7/2004 | Francischelli |
| 2004/0143260 A1 | 7/2004 | Francischelli |

(56) References Cited

U.S. PATENT DOCUMENTS

| | | |
|---|---|---|
| 2004/0186465 A1 | 9/2004 | Francischelli |
| 2004/0215183 A1 | 10/2004 | Hoey |
| 2004/0220560 A1 | 11/2004 | Briscoe |
| 2004/0236322 A1 | 11/2004 | Mulier |
| 2004/0267326 A1 | 12/2004 | Ocel |
| 2005/0010095 A1 | 1/2005 | Stewart et al. |
| 2005/0033280 A1 | 2/2005 | Francischelli |
| 2005/0070892 A1* | 3/2005 | Ciarrocca ............ A61B 18/148 606/46 |
| 2005/0090815 A1 | 4/2005 | Francischelli |
| 2005/0090816 A1 | 4/2005 | McClurken et al. |
| 2005/0143729 A1 | 6/2005 | Francischelli |
| 2005/0165392 A1 | 7/2005 | Francischelli |
| 2005/0171525 A1 | 8/2005 | Rioux et al. |
| 2005/0209564 A1 | 9/2005 | Bonner |
| 2005/0267454 A1 | 12/2005 | Hissong |
| 2006/0009756 A1 | 1/2006 | Francischelli |
| 2006/0009759 A1 | 1/2006 | Christian |
| 2006/0064085 A1 | 3/2006 | Schechter et al. |
| 2006/0106375 A1 | 5/2006 | Werneth et al. |
| 2006/0178670 A1* | 8/2006 | Woloszko ............ A61B 18/1402 606/48 |
| 2007/0049920 A1 | 3/2007 | McClurken et al. |
| 2007/0093808 A1 | 4/2007 | Mulier et al. |
| 2007/0118114 A1 | 5/2007 | Mulier et al. |
| 2007/0149965 A1 | 6/2007 | Gallo, Sr. et al. |
| 2007/0179495 A1 | 8/2007 | Salinas et al. |
| 2007/0208332 A1 | 9/2007 | Mulier et al. |
| 2008/0015563 A1 | 1/2008 | Hoey et al. |
| 2008/0058796 A1 | 3/2008 | O'Brien et al. |
| 2008/0071270 A1 | 3/2008 | Desinger et al. |
| 2008/0207208 A1 | 8/2008 | Schutz |
| 2008/0262489 A1 | 10/2008 | Steinke |
| 2009/0118729 A1 | 5/2009 | Auth et al. |
| 2009/0264879 A1 | 10/2009 | McClurken et al. |
| 2009/0306655 A1 | 12/2009 | Stagenes et al. |
| 2010/0022950 A1* | 1/2010 | Anderson ............ A61B 1/00114 604/100.01 |
| 2010/0087812 A1 | 4/2010 | Davison et al. |
| 2010/0100095 A1 | 4/2010 | McClurken et al. |
| 2010/0160906 A1 | 6/2010 | Jarrad |
| 2010/0241178 A1 | 9/2010 | Tilson et al. |
| 2011/0028965 A1 | 2/2011 | McClurken |
| 2011/0137298 A1 | 6/2011 | Nguyen et al. |
| 2011/0178515 A1 | 7/2011 | Bloom et al. |
| 2011/0196367 A1 | 8/2011 | Gallo |
| 2011/0295249 A1 | 12/2011 | Bloom et al. |
| 2011/0319889 A1 | 12/2011 | Conley et al. |
| 2012/0004657 A1 | 1/2012 | Conley et al. |
| 2012/0071712 A1 | 3/2012 | Manwaring et al. |
| 2012/0101496 A1 | 4/2012 | McClurken et al. |
| 2012/0116397 A1 | 5/2012 | Rencher et al. |
| 2012/0143293 A1 | 6/2012 | Mauch et al. |
| 2012/0151165 A1 | 6/2012 | Conley et al. |
| 2012/0157989 A1 | 6/2012 | Stone et al. |
| 2012/0172877 A1 | 7/2012 | Ryan et al. |
| 2012/0179158 A1 | 7/2012 | Stierman |
| 2012/0184983 A1 | 7/2012 | Chang et al. |
| 2012/0191084 A1 | 7/2012 | Davison et al. |
| 2012/0191117 A1 | 7/2012 | Palmer et al. |
| 2012/0215245 A1 | 8/2012 | Palmer et al. |
| 2012/0253343 A1 | 10/2012 | McClurken et al. |
| 2013/0053830 A1 | 2/2013 | Edwards et al. |
| 2013/0085498 A1 | 4/2013 | Matusaitis et al. |
| 2013/0331833 A1* | 12/2013 | Bloom ............ A61B 18/1445 606/33 |
| 2013/0345704 A1* | 12/2013 | Palmer ............ A61B 18/148 606/46 |
| 2015/0265337 A1 | 9/2015 | Bloom |
| 2016/0235468 A1 | 8/2016 | Prisco et al. |
| 2016/0235469 A1 | 8/2016 | Prisco et al. |
| 2016/0235474 A1 | 8/2016 | Prisco et al. |

OTHER PUBLICATIONS

Lee et al, Comparative Study on the Long-Term Effectiveness Between Coblation-and Microdebrider-Assisted partial Turbinoplasty, Laryngoscope 116:May 2006 pp. 729-734.

Berger et al., Histopathological Changes After Coblation Inferior Turbinate Reduction, Arch Otolaryngol Head Neck Surg. 2008;134(8):819-823.

Arthrocare PROcise EZ View Sinus Wand with integrated ablation, suction, and bipolar hemostasis (1 page) admitted prior art document.

* cited by examiner

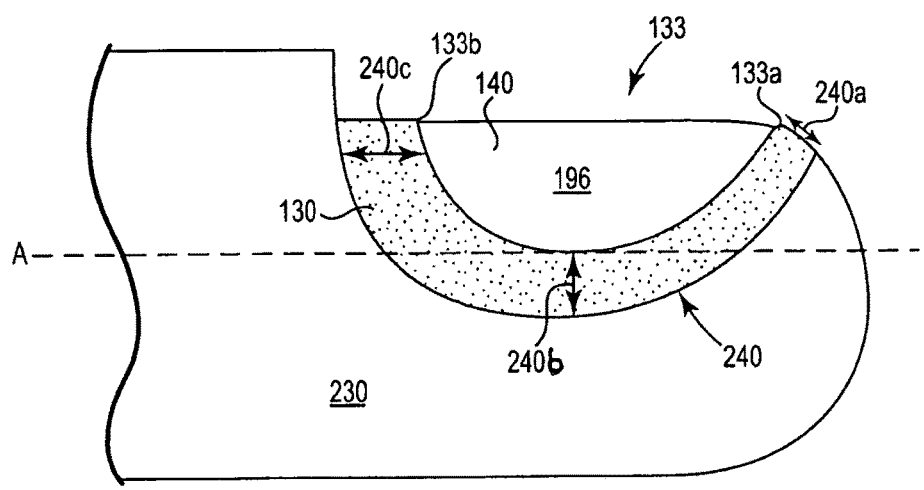
Fig. 8
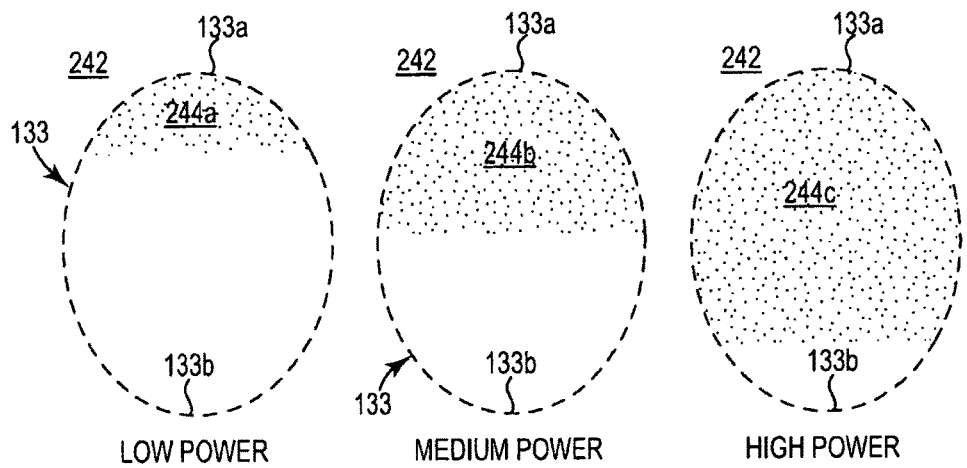
LOW POWER
Fig. 9A
MEDIUM POWER
Fig. 9B
HIGH POWER
Fig. 9C

ELECTROSURGICAL CUTTING INSTRUMENT

CROSS REFERENCE TO RELATED APPLICATIONS

This application claims the benefit of U.S. Provisional App. Ser. Nos. 61/920,412, filed Dec. 23, 2013 and 61/933,521, filed Jan. 30, 2014, the contents of which are both hereby incorporated by reference in their entirety.

BACKGROUND

The disclosure relates to instruments or tools used in performing surgery on a patient. More particularly, the disclosure relates to cutting instruments using electrodes to seal or cauterize tissue.

Clinicians use surgical instruments, including debriders such as microdebriders, to shave, cut, resect, abrade, or remove tissue, bone, or other body materials from a surgical site during surgery including endoscopic surgery. An example of such an instrument includes a rotating cutting blade on an elongated tube. The elongated tube is fit within an elongated outer tube having a cutting window exposing the cutting blade. The cutting blade is rotated within and with respect to the outer tube. The outer tube and inner tube are coupled to a handpiece. The handpiece typically includes a motor coupled to inner tube to rotate the cutting blade with respect to the handpiece. In one example, an actuator on the handpiece controls the rotation of the motor. A clinician is thus able to manipulate the location and rotation of the cutting blade to remove material from the surgical site. In some examples, a vacuum is applied through the inner tube to remove material that is cut with the blade. Many instruments also supply an irrigation fluid to the surgical site. The surgical instruments provide precise mechanical cutting at a surgical site through a low or minimally invasive incision or entry point in the patient.

One issue presented with surgical cutting instruments such as debriders involves the ability to control bleeding. If bleeding is not controlled, blood can obscure the view of the surgical site, adversely affect the precision of the cutting or severing tissue, and prolong the surgery. Too much blood loss can cause trauma to the patient that may require a blood transfusion. Electrosurgical instruments are often used to control bleeding in such circumstances. Electrosurgical instruments can be used to cauterize, coagulate/desiccate or simply reduce blood flow by controlling electrosurgical energy applied to the tissue. Small blood vessels, e.g., those having a diameter of less than about two millimeters, can be coapted through coagulation, i.e., the process of desiccating tissue where the tissue cells are ruptured and dried. Larger blood vessels may be coapted through sealing, i.e., the process of liquefying the collagen in the tissue so that it reforms into a fused mass. In some instances, a second surgical device is used to control bleeding either before or after body material is cut. Some electrosurgical cutting instruments include the ability to cut body material and control bleeding with the same device.

SUMMARY

This summary is provided to introduce a selection of concepts in a simplified form that are further described below in the Detailed Description. This summary is not intended to identify key features or essential features of the claimed subject matter, nor is it intended to be used to limit the scope of the claimed subject matter.

In one aspect, the disclosure is directed to an electrosurgical device having a tubular outer shaft and a tubular inner shaft. The tubular outer shaft includes an axis and a distal end region. The distal end region includes a distal-most tip and a cutting edge defining an outer shaft window proximal along the axis to the distal-most tip. The tubular inner shaft is coaxially maintained within the outer shaft such that the inner shaft is movable about the axis with respect to the outer shaft. The inner shaft includes an outer surface having a toothed edge defining an opening. The opening exposes an inner surface of the inner shaft in the window of the outer shaft when the opening is aligned with the window. A first electrode is disposed on the outer shaft in a region proximal along the axis to the window. A fluid distribution point is disposed on the outer shaft in a region proximal along the axis to the first electrode. The fluid distribution point emits fluid across the first electrode and toward the distal-most end. A second electrode electrically is isolated from the first electrode. The second electrode is disposed on the inner shaft and exposed in the window of the outer shaft. The second electrode includes a first portion disposed on the outer surface of the inner shaft and a second portion disposed on the inner surface of the inner shaft.

In another aspect, an electrosurgical device includes an outer shaft defining a lumen and a distal end defining a window in the outer shaft. An inner shaft is rotatably disposed within the lumen of the outer shaft. The inner shaft defines a distal portion, wherein the distal portion defines a cutting window in the inner shaft. A conductive ink trace is positioned on the outer shaft and an electrode is electrically connected to the conductive ink trace and positioned on the outer shaft such that insulating material is positioned between the inner shaft and the electrode.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated, as they become better understood by reference to the following detailed description. The elements of the drawings are not necessarily to scale relative to each other. Like reference numerals designate corresponding similar parts.

FIG. 8 is a schematic side view of a distal end region of an electrosurgical cutting device having a gap between electrodes that increases from a distal end to a proximal end of a cutting window.

FIGS. 9A-9C schematically illustrate effects created on tissue for varying levels of power using the distal end region illustrated in FIG. 8.

DETAILED DESCRIPTION

In the following Detailed Description, reference is made to the accompanying drawings, which form a part hereof, and in which is shown by way of illustration specific embodiments or examples in which the invention may be practiced. It is to be understood that other examples may be utilized and structural or logical changes may be made without departing from the scope of the present disclosure. The following detailed description, therefore, is not to be taken in a limiting sense, and the scope of the present invention is defined by the appended claims. It is to be understood that features of the various exemplary embodiments described herein may be combined with each other, unless specifically noted otherwise.

Surgical instruments such as debriders are suitable for a variety of surgical applications including ear, nose, and throat (ENT) procedures. Sinus procedures are challenging due to the proximal location of sensitive organs such as the eyes and brain and due to the small size of the surgical site. Example procedures include ethmoidectomies, turbinectomies, uncinectomies and others that can be used to target polyps and tumors.

Embodiments of electrosurgical cutting devices discussed below may comprise two modes: a cutting or debridement mode and a sealing or hemostasis mode and the two modes can be mutually exclusive, i.e., hemostasis is achieved via energy delivery to tissue while cutters of shafts are not active or cutting. As described in more detail below, the cutting or debridement mode includes rotation or oscillation of inner and outer shaft cutters to cut tissue positioned therebetween. In the hemostasis mode, energy may be advantageously delivered to electrodes simultaneously with a fluid such as saline to achieve an optimal tissue effect by delivering controlled thermal energy to tissue.

Figure 5:
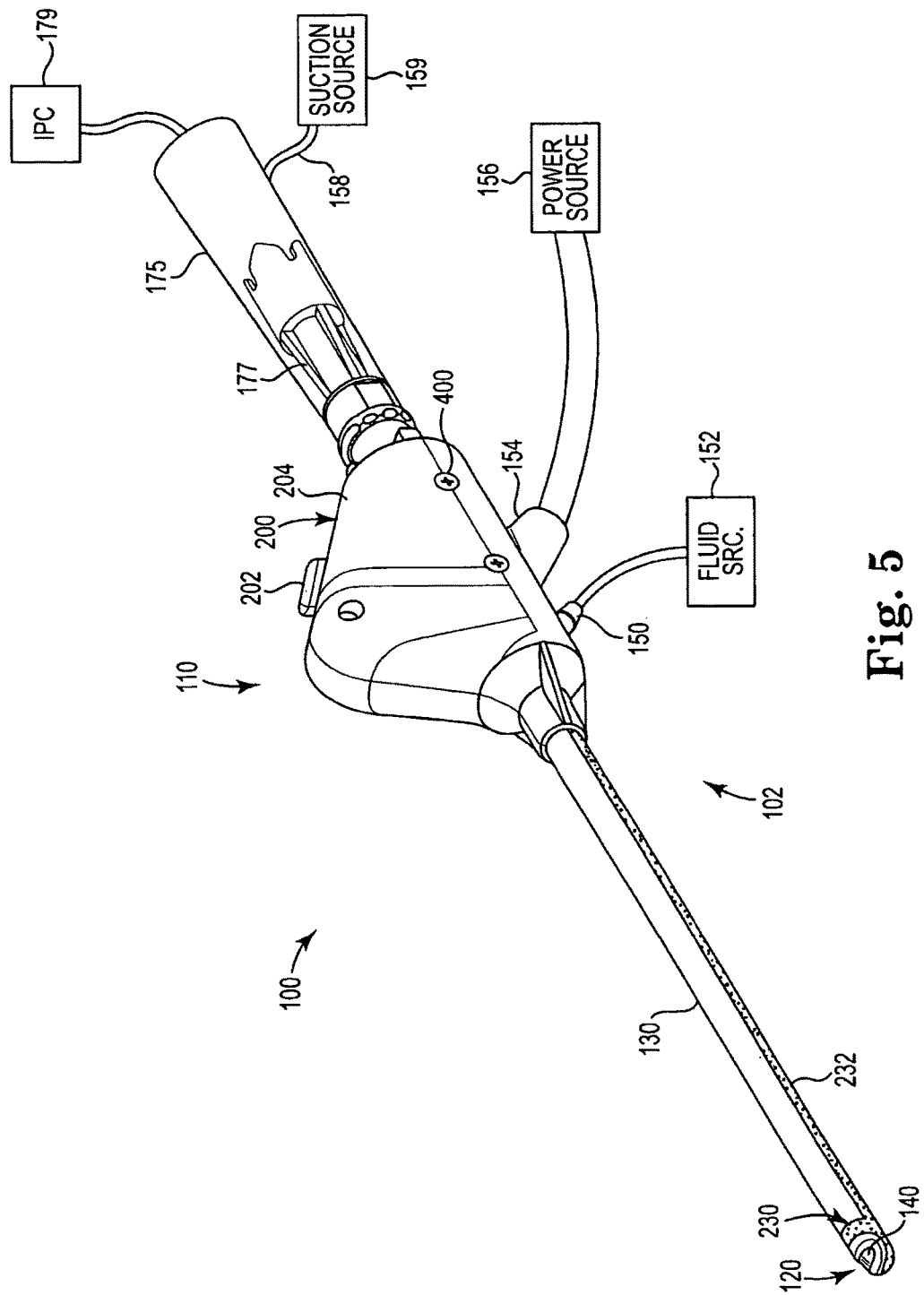
FIG. 5 is a schematic perspective view of another example system illustrating an electrosurgical cutting device.
Figure 6:
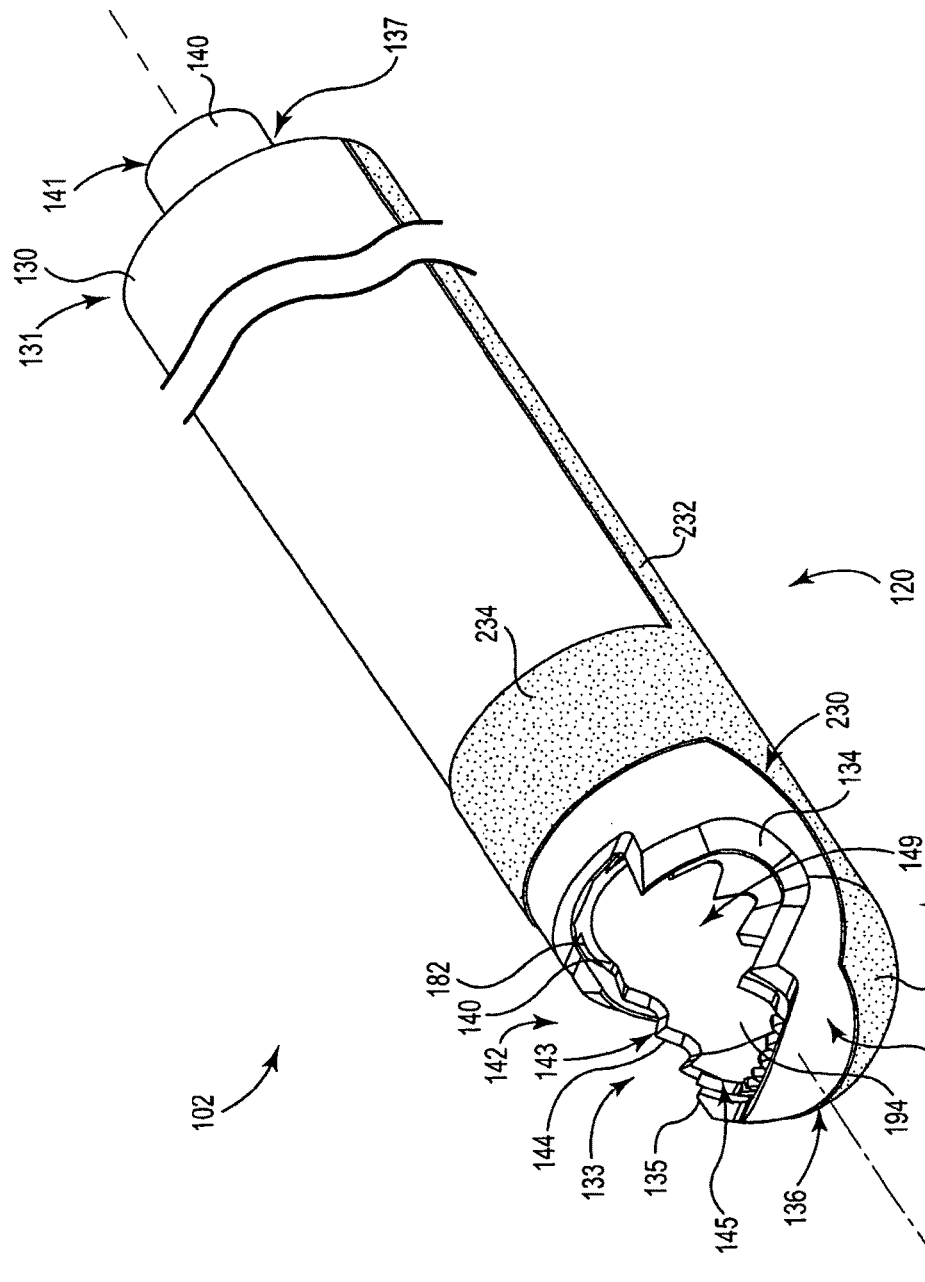
FIG. 6 is a schematic perspective view illustrating an example distal end region of the electrosurgical cutting device of FIG. 5 in a first configuration.
Figure 7:
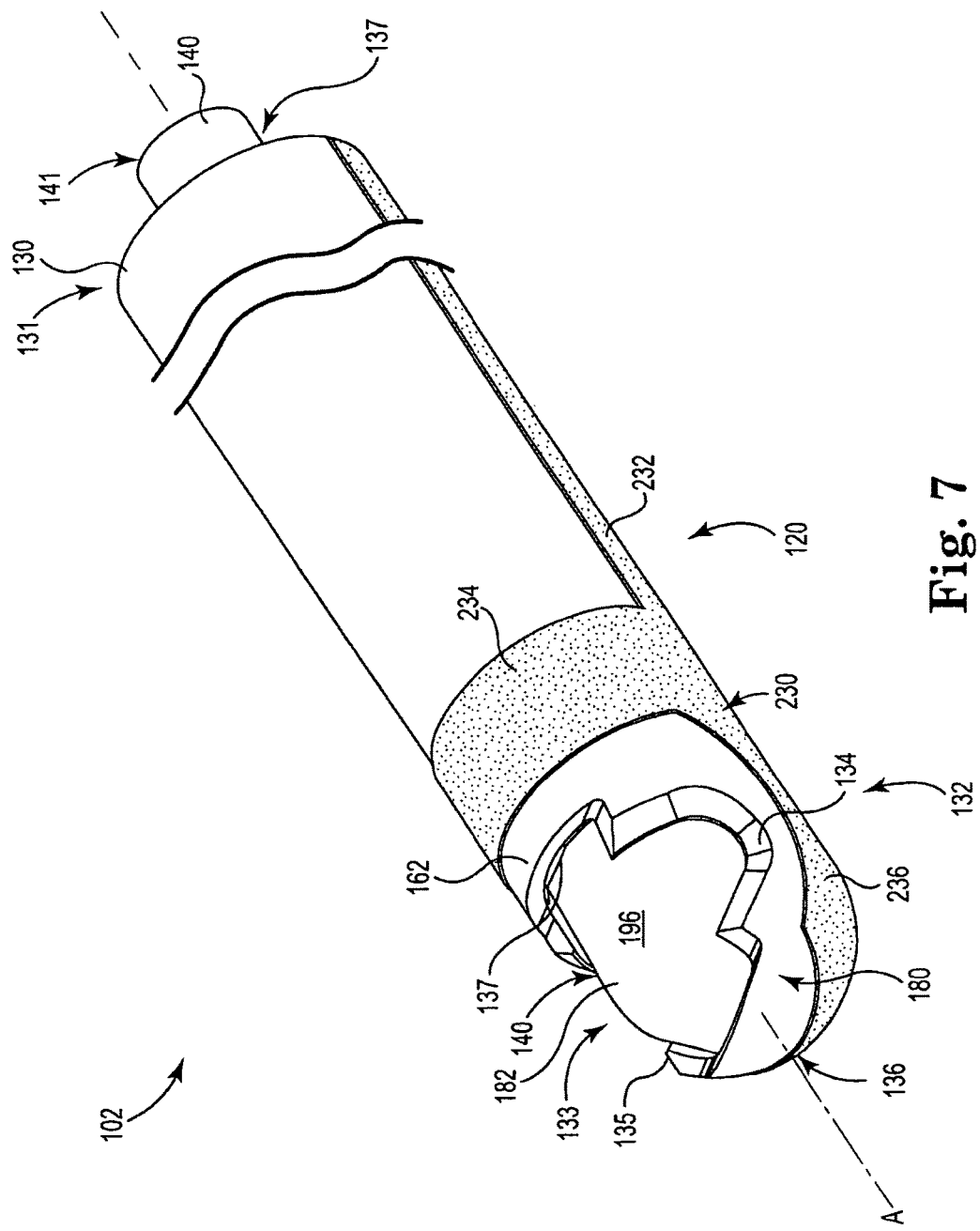
FIG. 7 is a schematic perspective view illustrating an example distal end region of the electrosurgical cutting device of FIG. 5 in a second configuration that is different than the first configuration.

In general, FIGS. 1-4 and associated description generally describe utilizing separate electrodes associated with inner and outer shafts, respectively, in the sealing or hemostasis mode. FIGS. 5-7 and associated description generally describe utilizing one electrode associated with the inner shaft and one electrode positioned external an outer shaft. FIGS. 8-14 and associated description describe additional features that can selectively be utilized within devices described herein.

During hemostasis mode, electrodes comprise bipolar electrodes and may comprise wet or dry electrodes. The electrodes may be used to deliver any suitable energy for purposes of coagulation, hemostasis or sealing of tissue. The electrodes are particularly useful with fluid such as saline provided by a fluid source which may be emitted near an outer shaft opening. In one embodiment, the outer shaft opening is fluidly connected to an outer shaft lumen (not shown) positioned between an interior surface of the outer shaft and an exterior surface of the inner shaft.

Other arrangements for carrying fluid to a distal end of devices can be used, for example an external lumen coupled external to the outer shaft and fluidly connected to the fluid source. In any event, fluid can be delivered to or proximate the opening of the outer shaft and interact with the electrodes. In this manner, the electrodes can advantageously provide Transcollation® sealing of tissue when used with the Transcollation® sealing energy supplied by the Aquamantys System, available from the Advanced Energy Division of Medtronic, Inc. With respect to "wet" RF coagulation technology, a variety of different technologies can be utilized, including technology for sealing tissue described in U.S. Pat. Nos. 6,558,385; 6,702,810, 6,953,461; 7,115,139, 7,311,708; 7,537,595; 7,645,277; 7,811,282; 7,998,140; 8,048,070; 8,083,736; 8,216,233; 8,348,946; 8,361,068; and 8,475,455 (the entire contents of each of which is incorporated by reference). These patents describe bipolar coagulation systems believed suitable for use in the present invention. Other systems for providing a source of energy are also contemplated.

When fluid from the fluid source is provided to the distal end, the fluid may travel between the outside diameter of the inner shaft and the inside diameter of the outer shaft to the distal end of the device. Fluid travels distally down the outer shaft and may "pool" in an area defined by the opening of outer shaft. Pooling of fluid at the electrodes allows for effective interaction between the fluid and the electrodes which in turn can provide effective and advantageous sealing of tissue, and in particular may provide effective Transcollation® sealing of tissue. Other approaches to fluid delivery can also be utilized.

Figure 1:
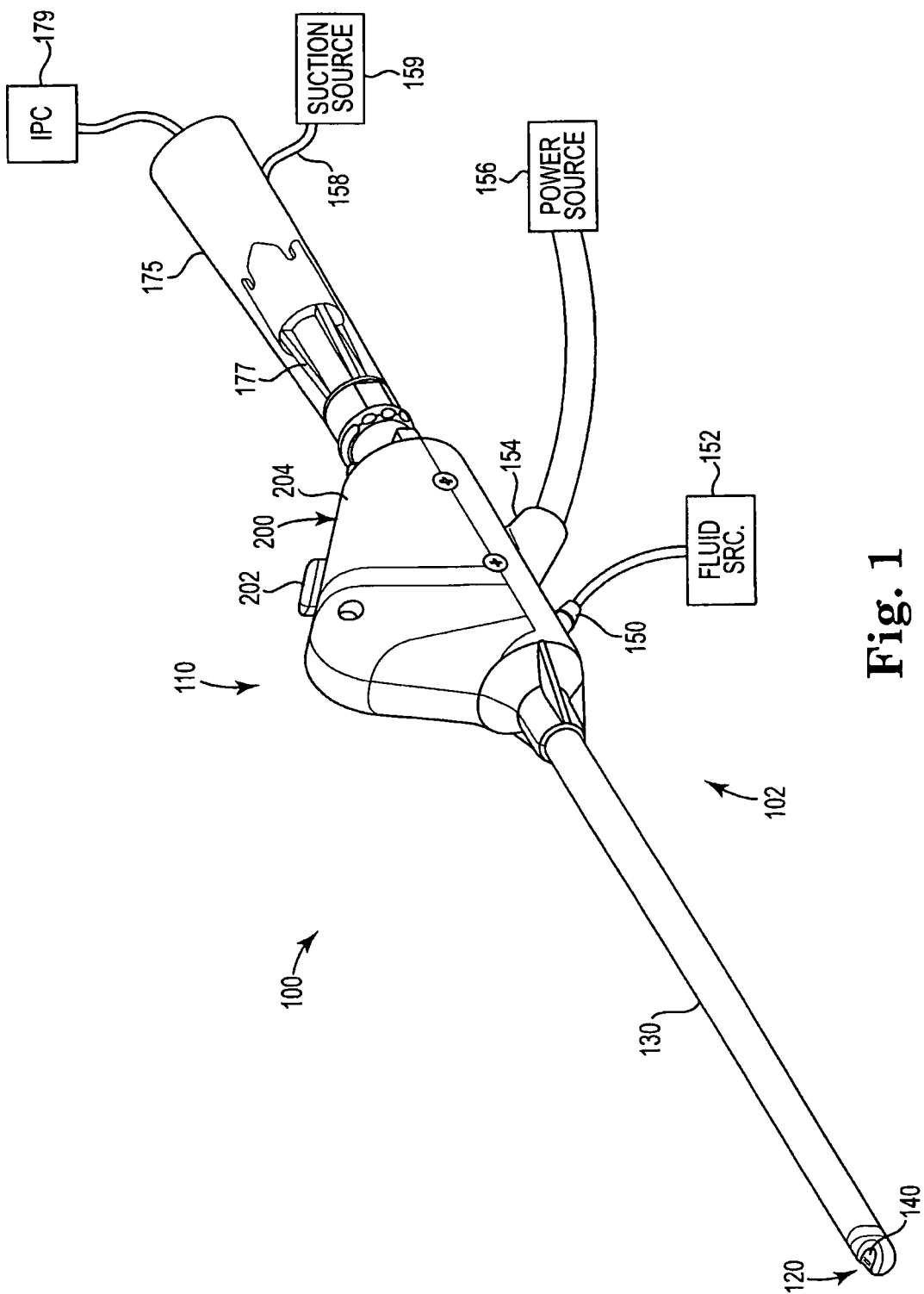
FIG. 1 is a schematic perspective view of a system illustrating an example electrosurgical cutting device.

With specific reference to FIG. 1 illustrates a system 100 that includes an electrosurgical device 102 having a proximal end region 110 and a distal end region 120. The device 102 includes tubular, or hollow, outer shaft 130 and a tubular, or hollow, inner shaft 140 coaxially maintained within the outer shaft 130. The distal end region 120 is configured to engage the surgical site. A portion of the inner shaft 140 is exposed at distal end region 120. The distal end region 120 includes a mechanical cutting element, such as a blade, and a bipolar electrode to provide for coapting blood vessels during hemostasis. In one example, at least the exposed portion of the inner shaft 140 is movable with respect to the outer shaft 130 to effect mechanical cutting at the surgical site. The distal end region 120 typically includes a low profile as it is often inserted through an incision in the patient.

In the example, proximal end region 110 includes a handle or handpiece 175 and an actuator 200 remote from the distal end 120 and thus remote from the surgical site such as outside of the patient. A clinician can grasp the handpiece 175 and can control the system 100 or operate the device 102 at least in part through the actuator. The actuator 200 includes a button 202 carried on a housing 204. In the example, the handpiece 175 and the actuator housing 204 are coupled together and affixed to the outer shaft 130 such that the outer shaft does not move with respect to the handpiece 175 and actuator housing 204. Examples are contemplated, however, where the outer shaft 130 can rotate with respect to the housing 204 and inner shaft 140.

The proximal end region 110 also includes a hub 177 coupled to inner shaft 140. In the example, the hub 175 is disposed within the handpiece 175 and is configured to move the inner shaft 140 with respect to the outer shaft 130. The device 102 may be coupled to a driving mechanism or motor, which may be included as part of an integrated power console, or IPC, 179 for driving the hub 177 and specifically for controlling rotation or oscillation of inner shaft 140 with respect to the handpiece 175.

Proximal end region 110 also includes a fluid source connector 150 for connection to a fluid source 152. In one example, the fluid source 152 can include a bag of fluid coupled to flexible delivery tubing to carry the fluid to connector 150. The fluid is conveyed along the shafts 130, 140 and is emitted from an opening at the distal end region 120. The hub 177 may be made isolated from the fluid source connector through the application of a silicon O-ring disposed around the inner shaft 140 proximal to the fluid source connector 150 and distal to the hub 177 or by other mechanisms. In one example, the fluid includes saline and can include physiologic saline such as sodium chloride (NaCl) 0.9% solution. Saline is an electrically conductive fluid, and other suitable electrically conductive fluids can be used. In other examples, the fluid may include a nonconductive fluid, such as deionized water, which may still provide advantages over using no fluid.

A pump (not shown) can be used to convey fluid from fluid source 152 to the electrosurgical device 102 and control fluid flow. In one example, delivery tubing is passed through the pump. The pump in one example is a peristaltic pump such as a rotary peristaltic pump or a linear peristaltic pump and can be used to convey the fluid through the delivery tubing by way of intermittent forces placed on the external surface of the delivery tubing. Peristaltic pumps are often preferred because the mechanical elements of the pump places forces are placed on the external surface of the delivery tubing and do not come into direct contact with the fluid, which can reduce the likelihood of fluid contamination. Other examples of system 100 might not include a pump, and fluid can be is provided to the electrosurgical device 102 via gravity.

Proximal end region 110 also includes a power source connector 154 for connection to a source of electrical energy indicated as power source 156. Power source 156 provides electrical energy, such as radio-frequency (RF) energy via insulated wires to the power source connector 154. The power source connector 154 is in electrical communication with conductors along the elongated portions of the shafts 130, 140 to electrodes at the distal end region 120. In one example, the elongated portions of the outer and inner shafts 130, 140 are conductive and carry the RF energy from the power source 156 to electrodes at the distal end region 120. In one example of power source 156 includes a generator configured for use with one or more electrosurgical devices. An example generator is available under the trade designation Aquamantys® and provides a type of RF sealing energy technology available under the trade designation Transcollation® from Medtronic Advanced Energy of Portsmouth, N.H., United States. Examples of suitable generators and flow rate controllers are described in U.S. Pat. No. 7,815,634, and published U.S. Pat. Application Nos. 2001-0032002; 2006-0149225 and 2005-0090816, which are incorporated by reference into this disclosure.

Proximal end region can also include a suction source connector 158 for connection to a suction source 159. The suction connector 158 is in fluid communication with an opening in the distal end region 120. Fragments of body materials cut with the device 102 and fluids can be removed from the surgical site through the opening in the distal end region via the suction source 159.

Figure 2:
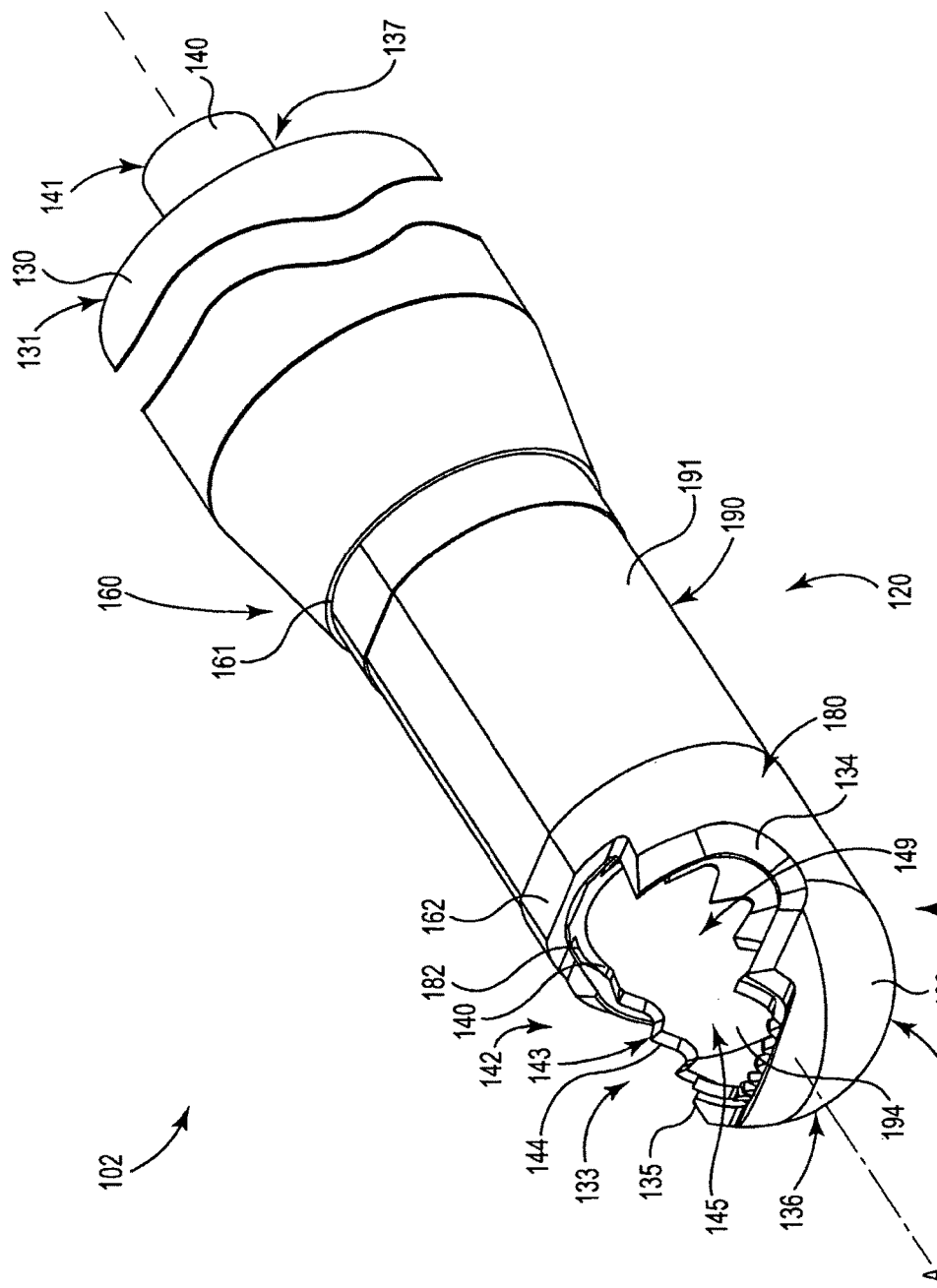
FIG. 2 is a schematic perspective view illustrating an example distal end region of the electrosurgical cutting device of FIG. 1 in a first configuration.
Figure 3:
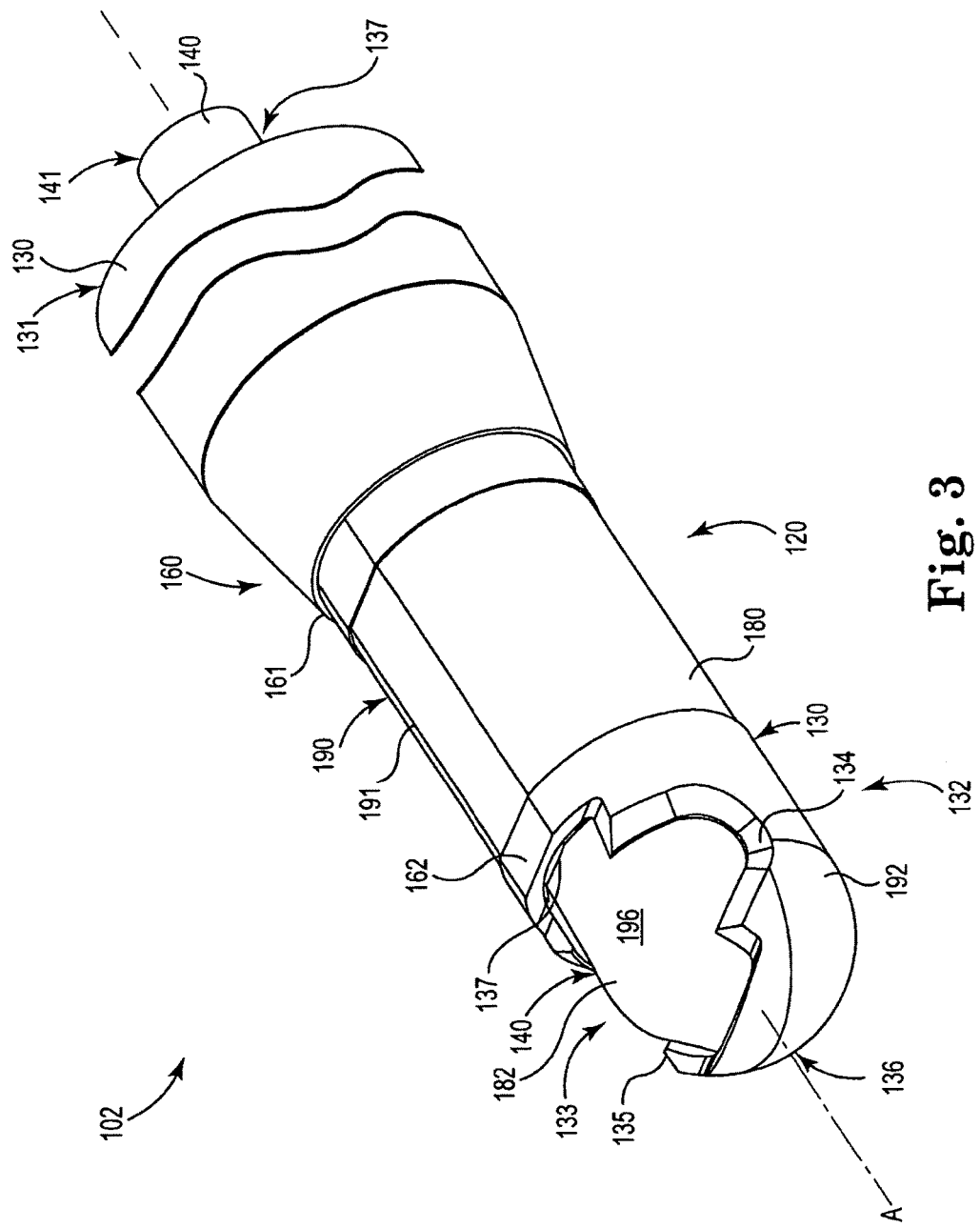
FIG. 3 is a schematic perspective view illustrating an example distal end region of the electrosurgical cutting device of FIG. 1 in a second configuration that is different than the first configuration.

FIGS. 2 and 3 illustrate schematic perspective views of outer shaft 130 and inner shaft 140 of device 102 in different configurations. In particular, FIG. 2 illustrates the device 102 with inner shaft 140 in a first open configuration with respect to outer shaft 130. FIG. 3 illustrates the device 102 with inner shaft 140 in a second closed configuration with respect to outer shaft 140.

FIGS. 2 and 3 illustrate elongated inner shaft 140 coaxially maintained within elongated outer shaft 130 along axis A. The outer shaft 130 includes an elongated portion that extends from a proximal end 131, which can be connected to housing 204, to a distal end 132 that includes an opening such as window 133 and a distal-most tip 136. An outer shaft cutting edge 134 defines window 133. In the example, the outer shaft cutting edge 134 includes cutting teeth 135. The outer shaft 130 may be rigid, malleable, or include combinations including a rigid portion and a malleable portion. The inner shaft 140 includes an elongated portion that extends from a proximal end 141, which can be connected to hub 177, to a distal end 142. A portion of the distal end 142 is exposed to the surgical site through window 133 of outer shaft 130.

A lumen 137 forms an irrigation channel between the outer shaft 130 and the inner shaft 140 that is configured to carry fluid between an outer surface of the inner shaft 140 and an inner surface of the outer shaft 130. Fluid is emitted from the distal end region 120 at distribution point 160. In one example, the outer shaft 130 includes more than one distribution points, such as proximal distribution point 161 and distal distribution point 162 that are spaced-apart from each other. In the example, distribution points 161 and 162 are aligned along longitudinal axis A on the outer surface 180 of the outer shaft 130. Fluid from distribution point 161, as well as distribution point 162, generally flows axially along the outer surface 180 towards window 133 of the outer shaft 130.

One or more outer shaft electrodes 190 can be disposed along the outer surface 180 of the outer shaft 130 in the distal end region 120. In the example, an electrode 191 is exposed on the outer surface 180 of the outer shaft 130 between fluid distribution point 161 and the window 133 of the outer shaft 130 in the path of fluid flow. More particularly, the electrode 191 can be exposed on the outer surface 180 between proximate fluid distribution point 161 and distal distribution point 162. The electrode 191 can be formed as a patch of a conductive element in electrical communication with the power source connector 150 or, as illustrated, a conductive element along the entire circumference of the outer surface 180 between the distribution point 161 and window 133.

The electrode 191 can also be in electrical communication with a second electrode 192 disposed around the distal-most tip 136 and on the outer surface 180 of the outer shaft 130 opposite from window 133. Electrode 192 in the example on the outer surface 180 is spaced-apart from outer shaft cutting edge 134. In the example, electrodes 191 and 192 are configured to be part of the same active pole or return pole.

FIG. 2 illustrates inner shaft 140 in a first configuration, or open position, with respect to outer shaft 130 such that an inner shaft cutting edge or inner cutter 143 is exposed to window 133. Inner cutter 143 includes cutting teeth 144 and defines an inner shaft window or opening 145. An inner surface 182 of the inner shaft 140 is exposed to the surgical site in the open position. The inner surface 182 defines a lumen 149 axially extending along the elongated inner shaft 140. Fluid from distribution point 161 and distribution point 162 can collect on the inner surface 182 of the inner shaft 140 within lumen 149.

The device 102 can be used to remove body matter and fluids from the surgical site while the outer and inner shaft cutters 134 and 143 are the open position. For example, the inner shaft and outer shaft cutters 134, 143, respectively, may move relative to one another in oscillation, rotation, or both, via the hub 177 to mechanically cut body matter. In one example, outer shaft cutter 134 may remain stationary relative to the handpiece 175 and actuator housing 204 while the inner shaft cutter 143 rotates about longitudinal axis A of the device to cut body matter. Also, the outer shaft 130 and the inner shaft 140 can be locked in the open position. The clinician can also manipulate the device 102 so that the distal end region moves along the longitudinal axis A, rotates about the longitudinal axis A, or otherwise to cut body matter with teeth 144 without rotating the inner shaft 140 with respect to the outer shaft 130.

The inner shaft opening 145 is fluidly connected to an inner shaft lumen 149 that extends from the inner shaft opening 145 to the proximal end 141 of inner shaft 140 and may be fluidly connected with the suction source 159 through suction source connection 158. When the inner shaft 140 is in the open position, body matter cut via inner and outer shaft cutters 143, 134 and fluid, such as fluid emitted from distribution points 161 and 162 is aspirated into the inner shaft lumen 149 through the inner shaft opening 145 upon application of suction source 159 to remove body material and fluid from the surgical site.

One or more electrodes, such as inner shaft electrode 194 can be disposed on the inner surface 182 of the inner shaft 140 in the distal end region 120. In the example, electrode 194 is exposed on the inner surface 182 of inner shaft 140 in the region axially distal to the distal fluid distribution point 162 on the outer surface 180 of the outer shaft 130. In another example, the electrode 194 is exposed on inner surface 182 of the inner shaft 140 in the region at least distal to the proximal-most inner shaft edge 143 or proximal-most portion of the inner shaft window 145. In one example, the inner shaft electrode 194 is electrically isolated from the outer shaft electrode 190, such as electrodes 191 and 192. In another example, the outer shaft 130 is electrically isolated from the inner shaft 140. The inner shaft electrode 194 is in electrical communication with the power source connector 150 and forms an electrode pole opposite the pole of the outer surface electrode 190. For example, if the outer surface electrode 190 is the active electrode then the inner surface electrode 194 is the return electrode in the bipolar configuration.

FIG. 3 illustrates the inner shaft 140 in a second configuration, or closed position, with respect to the outer shaft 130. Inner shaft 140 is rotated about longitudinal axis A within the outer shaft 130 such that the inner shaft cutter 143 is completely shielded from exposure. For example, the inner shaft in the closed position can be rotated 180 degrees with respect to inner shaft relative to the outer shaft in the open position. The inner shaft cutter 143 in one example, is facing the interior of the outer shaft 130 opposite from the outer shaft window 133 and an outer surface 184 of the inner shaft 140 is exposed in the window 133. In some examples, the longitudinal edges of window 133 do not extend 180 degrees radially around the circumference of the outer shaft 130. In this case, the inner shaft 140 can be rotated less than 180 degrees from the open position to be in the closed position. In one example, the inner shaft 140 can be locked in the closed position.

One or more electrodes, such as electrode 196, can be disposed on the outer surface 184 of the inner shaft 140. In the example, electrode 196 is exposed in the window 133 while the inner shaft 140 is in the closed position. In the example, electrode 196 is exposed on the outer surface 184 of inner shaft 140 in the region axially distal to the distal fluid distribution point 162 on the outer surface 180 of the outer shaft 130. In another example, the electrode 196 is exposed on outer surface 184 of the inner shaft 140 in the region at least longitudinally distal to the proximal-most inner shaft edge 143 or proximal-most portion of the inner shaft window 145. In one example, the electrode 196 on the outer surface 184 is in electrical communication with shaft electrode 194 on the inner surface 182 of the inner shaft 140. Electrode 196 is also electrically isolated from the outer shaft electrode 190, such as electrodes 191 and 192. Electrodes 194, 196 are in electrical communication with the power source connector 150 and form an electrode pole opposite the pole of the outer surface electrode 190. For example, if the outer surface electrode 190 on the outer shaft 130 is the active electrode then the electrodes 194, 196 on the inner shaft 140 are the return electrodes in the bipolar configuration.

In one example, RF energy is delivered to tissue through electrodes while the inner shaft 140 is in the closed position without attendant risk that the cutting teeth 144 of the inner shaft 140 will diminish the efforts to achieve hemostasis. Device 102 may thus comprise two modes: a cutting or debridement mode and a sealing or hemostasis mode and the two modes may be mutually exclusive. In other words, hemostasis is achieved via RF energy delivered to tissue while cutters 134, 143 are not active or cutting. Further, RF energy may be advantageously delivered simultaneously with the fluid such as saline to achieve an optimal tissue effect by delivering controlled thermal energy to tissue. In other examples, RF energy may be delivered to electrodes during cutting mode while the cutters 134, 143 are actively cutting so that cutting or debridement mode is not exclusive of sealing or hemostasis mode. Still further, the inner shaft 140 may be locked in an open position during sealing or hemostasis mode in order for fluid to collect and be suctioned from lumen 149.

Figure 4:
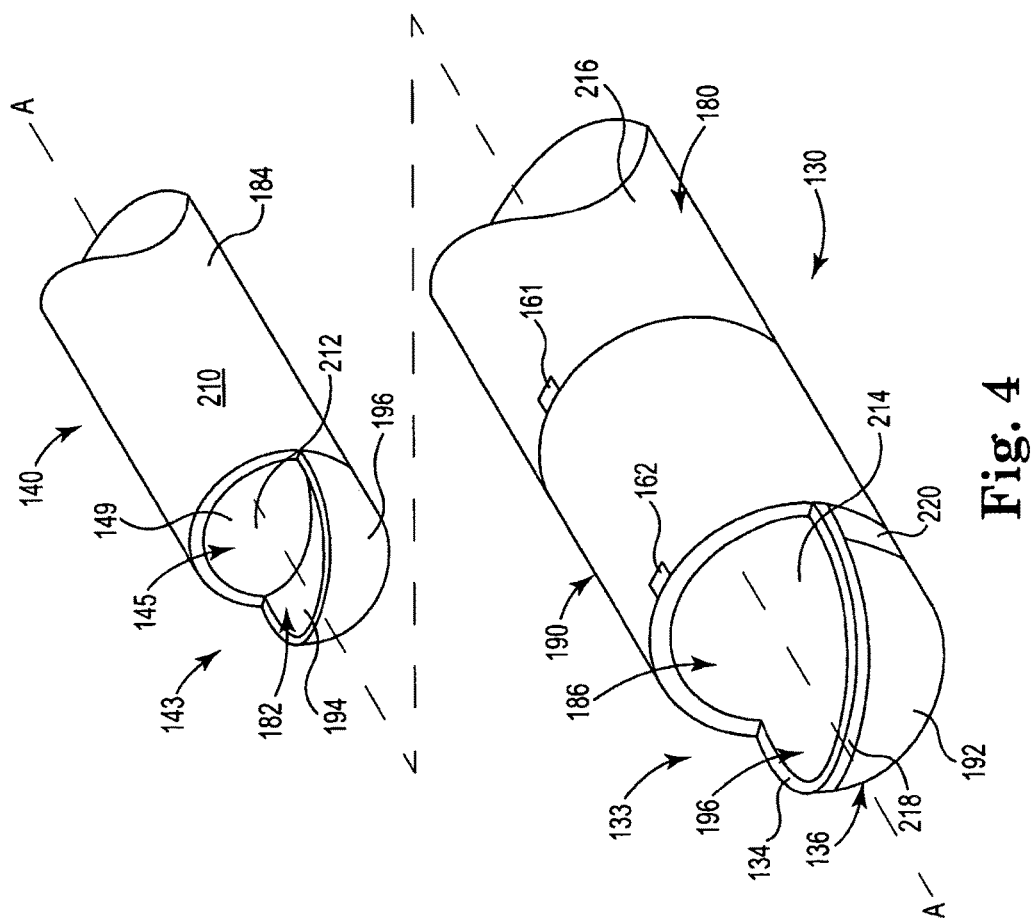
FIG. 4 is schematic exploded view illustrating features of components of the electrosurgical cutting device of FIG. 1.

FIG. 4 schematically illustrates outer shaft 130 and inner shaft 140. Inner shaft 140 includes inner cutter 143 defining inner shaft opening 145, as illustrated schematically. Inner shaft 140 also includes inner surface 182 forming lumen 149 and outer surface 184. The inner surface 182 exposes inner surface electrode 194 and outer surface 184 exposes outer surface electrode 196. Outer shaft 130 includes distal-most tip 136 and cutting edge 134 to define window 133, also as illustrated schematically. Outer shaft 130 also includes outer surface 180 and, as illustrated, inner surface 186.

Inner and outer shafts 130 and 140 are preferably constructed from a metal such as titanium, copper, tantalum, molybdenum, tungsten, or stainless steel, or another conductive material that can withstand forces used to cut body materials and repeated sterilizations in high temperature autoclaves or other suitable medical-grade materials. If the shafts 130, 140 are intended for single use, shafts 130, 140 can be constructed from a conductive medical-grade material that can withstand forces used to cut body materials and temperatures used in hemostasis.

Inner and outer shafts 130 include an electrically isolating material capable of withstanding use and cleaning conditions. The conductive inner and outer surfaces 182, 184 of the inner shaft 140 are selectively covered with an insulator 210, 212, respectively. The conductive outer and inner surfaces 180, 186 of the outer shaft 130 are selectively covered or coated with an insulator 214, 216, respectively. Insulators 210, 212, 214, 216 can be one or more medical-grade insulating polymer formed from fluorinated ethylene propylene (FEP), polytetrafluoroethylene (PTFE), parylene or any other material suitable as a non-conductive or electrically insulative material. In one example, the coating includes polyaryletherketones (PAEK) polymer thermoplastic such as polyetheretherketone (PEEK) polymer thermoplastic. One particularly suitable and medical-grade PEEK polymer thermoplastic coating is available under the trade designation Vicote from Victrex Manufacturing Ltd. of Thorton Cleveleys, Lancashire, United Kingdom. The polymer thermoplastic can be dispersed on the surfaces 180, 182, 184, and 186 as either a powder or aqueous solution to form coatings on the surfaces 180, 182, 184, and 186.

Electrodes, such as electrodes 190 (electrodes 191, 192), 194, and 196, are formed on the outer and inner shafts 130, 140. In one example, the region of outer and inner shafts 130, 140 are configured to serve as electrodes and are not coated. In one example, the not coated regions are masked during the coating and the masks are later removed to expose uncoated regions of the shafts 130, 140 configured to act as electrodes. In another example, the shafts 130, 140 are coated, and the coating is later removed from shafts 130, 140 to exposed the regions configured to act as electrodes. Still further, some combination of masking and coating removal is used to form the not coated regions configured to act as electrodes.

FIG. 4 illustrates an example where the entire inner surface 186 of outer shaft 130 is coated with an insulator 214 thus electrically isolating the outer shaft 130 from the inner shaft 140. The outer surface 180 of the outer shaft 130 is coated along the elongated portion to the proximal end 131 with insulator 216. At the distal end region 120, the outer surface 180 of the outer shaft 130 is exposed and not coated between about the fluid distribution point 161 and the window 133. Alternatively, the outer surface 180 can be exposed and not coated between the fluid distribution points 161, 162. FIG. 4 illustrates the entire circumference of the outer surface 180 is exposed and not coated from the fluid distribution point 161 to the window 133.

FIG. 4 also illustrates an example where the outer surface 180 of the outer shaft 130 around distal-most tip 136 and the side opposite window 133 is exposed and not coated forming electrode 192. Electrode 192 is illustrated as spaced-apart from window 133 by a strip of coating serving as insulator 218 along the distal parts of the cutting edge 134. In one example, an insulator 219 at least partially separates electrodes 191 and 192.

In the examples above, the inner shaft 140 is electrically isolated from the outer shaft 130, and the inner shaft 140 can be left uncoated. In one example, however, the inner and outer surfaces 182, 184 of inner shaft 140 are coated to help focus the RF field and to electrically isolate the hub 177 from the inner shaft 140. In one example, the elongated portions of the inner and outer surfaces 182, 184 of inner shaft 140 are left coated. In the distal end region 120, the inner and outer surfaces 182, 184 include exposed and not coated region 226.

Electrodes are formed from the exposed and not coated regions. In one example, a conductive metal can be affixed to the exposed and uncoated regions to serve as electrodes 190 (electrodes 191, 192), 194, and 196. In another example, the exposed and not coated regions can serve as the electrodes themselves. In the preferred example, the exposed and not coated regions serve as the electrodes, and the inner shaft 140 is disposed within the outer shaft 130 during construction of the device 102. Energized electrodes and the fluid dispersed from distribution points 161 or 161 and 162 combine to form a field of RF energy that extends 360 degrees around the distal end region 120 and further distal to the distal-most tip 136 to coapt blood vessels during hemostasis.

FIG. 5 illustrates an alternative example embodiment of system 100 including an alternative embodiment of device 102 having proximal end region indicated generally at 110 and distal end region indicated generally at 120. FIGS. 6 and 7 illustrate schematic perspective views of the distal end region 120 having outer shaft 130 and inner shaft 140 of device 102 in different configurations. In particular, FIG. 6 illustrates the device 102 with inner shaft 140 in a first open configuration with respect to outer shaft 130. FIG. 7 illustrates the device 102 with inner shaft 140 in a second closed configuration with respect to outer shaft 140. In the illustrated embodiment, a bipolar electrode configuration is utilized to deliver the RF energy, with the electrodes 194 and/or 196 of the inner shaft 140 serving as a first electrode and an outer electrode 230, positioned on an outer surface of outer shaft 130, serving as a second electrode. Electrode 230 is electrically coupled to the power source 156 through a trace or lead 232 connected to source connector 154.

There are various different arrangements for connection between the source connector 154 and each of the electrodes 194/196 and 230. In one embodiment, cell 200 maintains one or more clips that provide independent electrical connection to the electrodes 194/196 and 230. In an alternative embodiment, connector 154 can include an external wire that electrically couples to trace 232 while cell 200 maintains a connection to electrode 194/196. Regardless of the particular connection arrangement, electrodes 194/196 and 230 create a bipolar arrangement such that RF energy can be delivered to tissue proximate the distal end portion 120. In such an arrangement, one of the electrodes 194/196, 230 serves as a source electrode whereas the other of the electrodes 194/196, 230 serves as a return electrode. Tissue proximate the end portion serves to complete a circuit that includes the electrodes 194/196, 230. Current flowing through this tissue assists in promoting hemostasis of the tissue.

Similar to the examples above, the outer shaft 130 may be rigid or malleable or combinations thereof and may be made of a variety of metals and/or polymers or combinations thereof, for example may be made of stainless steel. In one embodiment, the outer shaft 130 is coated with a suitable insulating material such as a hydrophobic polymer. Example insulating materials include parylene, fluorinated ethylene propylene (FEP), polytetrafluoroethylene (PTFE), or any other material suitable as a non-conductive or electrically insulative material. In an alternative embodiment, the outer shaft 130 is formed of an insulating material. The conductive trace 232 is applied to the outer shaft 130 such that the insulating material is positioned between the conductive trace 232 and the outer shaft 130. To this end, the electrode 230 and conductive trace 232 are electrically insulated from the inner shaft 140. Conductive trace 232 can be formed of various suitable conductors as desired. In one embodiment, the outer shaft 130 includes an outer insulating layer and the conductive trace 232 is a flexible circuit formed of a conductive ink (e.g., silver, copper, nickel, gold and/or combinations thereof) that is printed directly on the insulating layer of the outer shaft 130.

The conductive trace 232, in one embodiment, can further be coated with a suitable insulating material as discussed above, so as to prevent unintended transfer of electrical energy proximate the trace 232. When a conductive ink is used to form the electrode 230 and conductive trace 232, a suitable mask can be used to cover the electrode 230 prior to coating trace 232 with an insulating material. As such, a portion not coated with the insulating material forms the electrode 230.

In the embodiment illustrated, electrode 230 defines a proximal band 234 coupled to trace 232 and extending continuously around the outer shaft 130. In other embodiments, band 234 extends partially around outer shaft 130. For example, the band 234 can extend around 90°, 120°, 180°, 240°, 270° or other value about the outer shaft 130, when viewed from distal tip 136. In any event band 234 is positioned proximal the window 133 in the illustrated embodiment. Extending from the band 234 is a distal extension 236 that is coupled with the band 234 so as to control the current density applied to tissue proximate electrode 230. The distal extension 236 illustratively extends around a lower circumference of the outer shaft 130 and extends proximate the cutting window 133. As desired, distal extension 236 can be configured to cover a portion of the outer shaft 130 proximate the cutting window 133 or extend to encompass an entirety of the outer shaft 130 without creating a continuous connection with the inner shaft 140, and in particular the electrodes 194/196. In one embodiment, electrode 230 is formed of a conductive ink (e.g., silver, copper, nickel, gold and/or combinations thereof) that is printed onto outer shaft 130. In addition, portions of electrode 230 can be coated with an insulating material as desired to alter delivery of electrical energy through electrode 230.

Electrode 230 can be sized to define a surface area that controls an amount of current density applied to tissue that comes into contact or is proximate electrode 230 during delivery of RF energy. Electrode 230 can further be positioned on outer shaft 130 in various positions and be formed by various sizes as desired. For instance, the electrode 230 can be positioned such that a portion or an entirety of the electrode 230 is proximal the window 133 along axis A. The electrode 230 can be formed on a top of outer shaft 130 on the same side as the window 133. In other instances, the electrode 230 can extend both proximal and distal the window 133. In a further embodiment, electrode 230 is spaced apart from the distal tip 136 and in a specific embodiment an entirety of the electrode 230 is proximal a distal-most portion of window 133. The distal extension 236, in one embodiment, is shaped to follow a contour of window 133, or otherwise establish a uniform spacing between the electrode 230 and the electrode 196. In a specific embodiment, the electrode 230 is uniformly spaced from the inner shaft 140, providing a gap between an edge of the electrode 230 and an edge of the cutting window 133 (and thus electrode 196). The uniform space or gap between the electrode 230 and the inner shaft is 0.04 inches, in one embodiment, which assists in providing a desired tissue impedance and reduces sensitivity to relative orientation between window 133 and target tissue.

Having described different embodiments generally shown in FIGS. 1 and 5, FIGS. 8-14 illustrate various alternative features that can be used in these embodiments, either singularly or in combination. In one example feature, schematically illustrated in FIG. 8, a gap 240 (e.g., comprised of an insulating material) between the electrode 196 and the electrode 230 (i.e., about window 133) is selected to vary along axis A from a distal end 133a of the window 133 to a proximal end 133b of the window so as to change an effect on tissue created between the electrodes 196 and 230 during delivery of electrical energy. In the illustrated embodiment, a width of the gap 240 (i.e., a minimum distance between electrodes 196 and 230) increases from a first distal width 240a at the distal end 133a, to a second intermediate width 240b to a third proximal width 240c at the proximal end 133b. The first width 240a positioned at the distal end 133a is the smallest gap, whereas the second width 240b positioned proximal the distal end 133a is larger than the first width 240b and the third width 240c positioned at the proximal end 133b is larger than the second width 240b. Due to the varying widths between the electrodes 196 and 230, the effect on tissue will vary.

As schematically illustrated in FIGS. 9A-9C, when using the varying gap 240, the effect on tissue can vary by the power delivered to a target site 242 when the window 133 (illustrated in dashed lines to relative positioning between the target site 242 and the window 133). In particular, illustrated is an effect using a low power delivery (FIG. 9A), a medium power delivery (FIG. 9B) and a high power delivery (FIG. 9C). In FIG. 9A, the low power delivered to one of the electrodes 196/230 (i.e., to the active electrode) is sufficient to create an effect 244a that is a small portion of the window 133, concentrated at the distal end 133a. As power is increased to medium power illustrated in FIG. 9B, an effect 244b is created that is larger than effect 244a. Further still, upon increasing to high power illustrated in FIG. 9C, an effect 244c is created that is larger than both effect 244a and 244b. The effects 244a-244c created are a function of the widths 240a-240c, respectively. As more power is provided to the active electrode, a larger amount of energy can be delivered through tissue of the target site 242. As such, a larger effect is created.

Figure 10A:
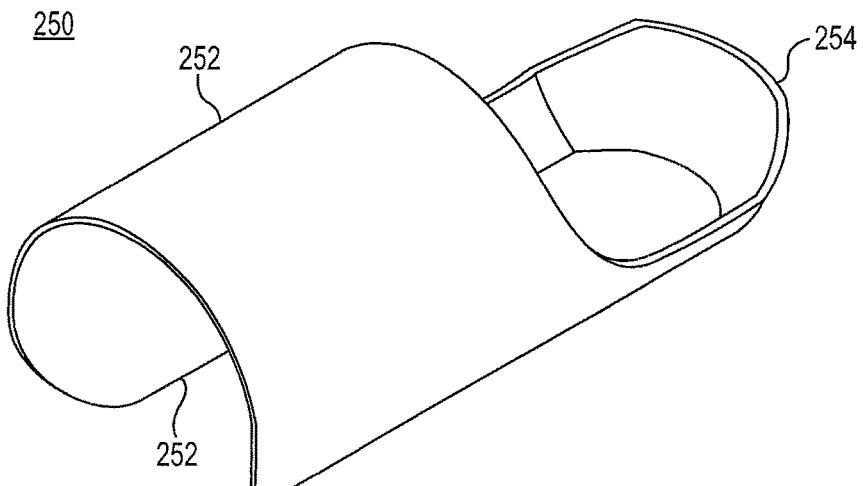
FIGS. 10A-10C are different views of an example electrode formed prior to assembly to an outer shaft of a device.
Figure 10B:
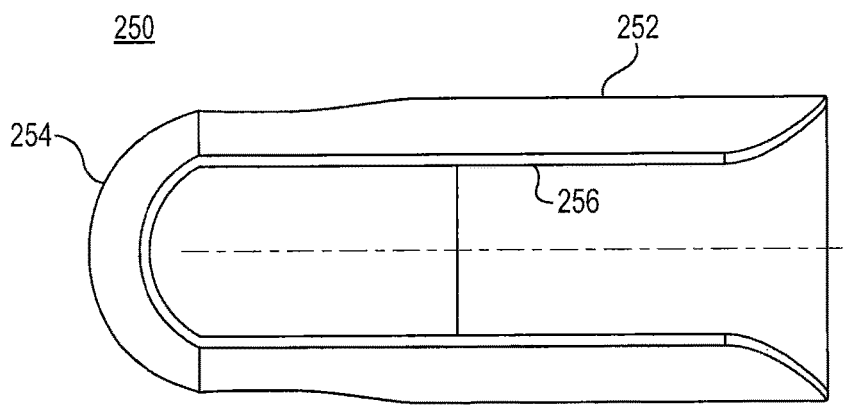
Figure 10C:
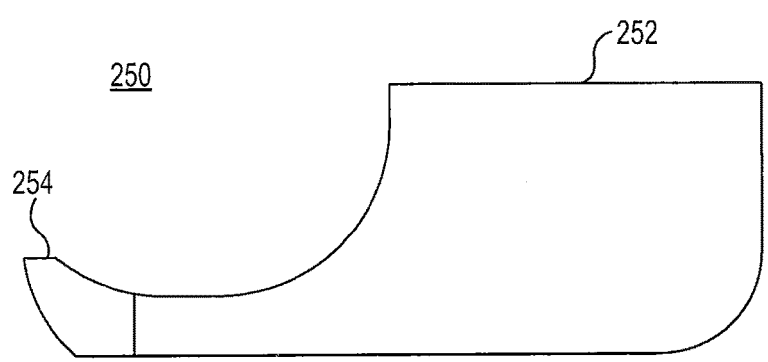

Another alternative feature includes an electrode positioned on outer shaft 130 that is formed prior to coupling with the outer shaft 130. For example, FIGS. 10A-10C illustrate an alternative electrode 250 formed of a unitary body and assembled to outer shaft 130. Electrode 250 is similar to electrode 230, forming a proximal band 252 and distal extension 254 coupled to the band 252. The distal extension 254 can be formed to create a uniform gap with a corresponding window 133 or to create a varying gap with the corresponding window 133 as discussed above. During assembly, electrode 250 is positioned over a distal end of the outer shaft 130 and a conductive trace (not shown) is positioned on the outer shaft 130 and electrically coupled to the electrode 250. As illustrated, electrode 250 partially extends around an outer diameter of the outer shaft 130 and defines a slot 256. The slot 256 is positioned over the shaft 130 to assemble the electrode 250 to the shaft 130. Electrode 250 can be formed of various conductive materials such as copper, copper alloys and the like.

Figure 11:
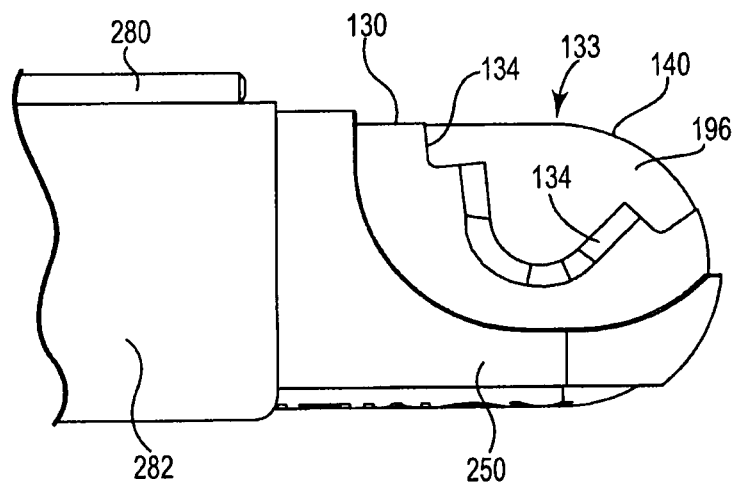
FIG. 11 is a side view of an example distal end region of an electrosurgical cutting device having external tubing forming an irrigation channel for fluid delivery.

In one example alternative of fluid delivery, shown in FIG. 11, fluid is provided external to the outer shaft 130, with electrode 250 (FIGS. 10A-10C) coupled thereto and inner shaft 140 positioned within the outer shaft 130 as discussed above. External tubing 280 forms an irrigation channel to deliver fluid to the distal end region. A heat shrink tubing 282 are applied to outer shaft 140. In particular, heat shrink tubing 282 is positioned over electrode 250 and outer shaft 130 to secure electrode 250 to outer shaft 130. Tubing 280 (e.g., formed of a hypotube) is positioned along the heat shrink tubing 282 and is positioned to deliver fluid proximate window 133. The tubing 280 can be used with various embodiments discussed above.

Figure 12:
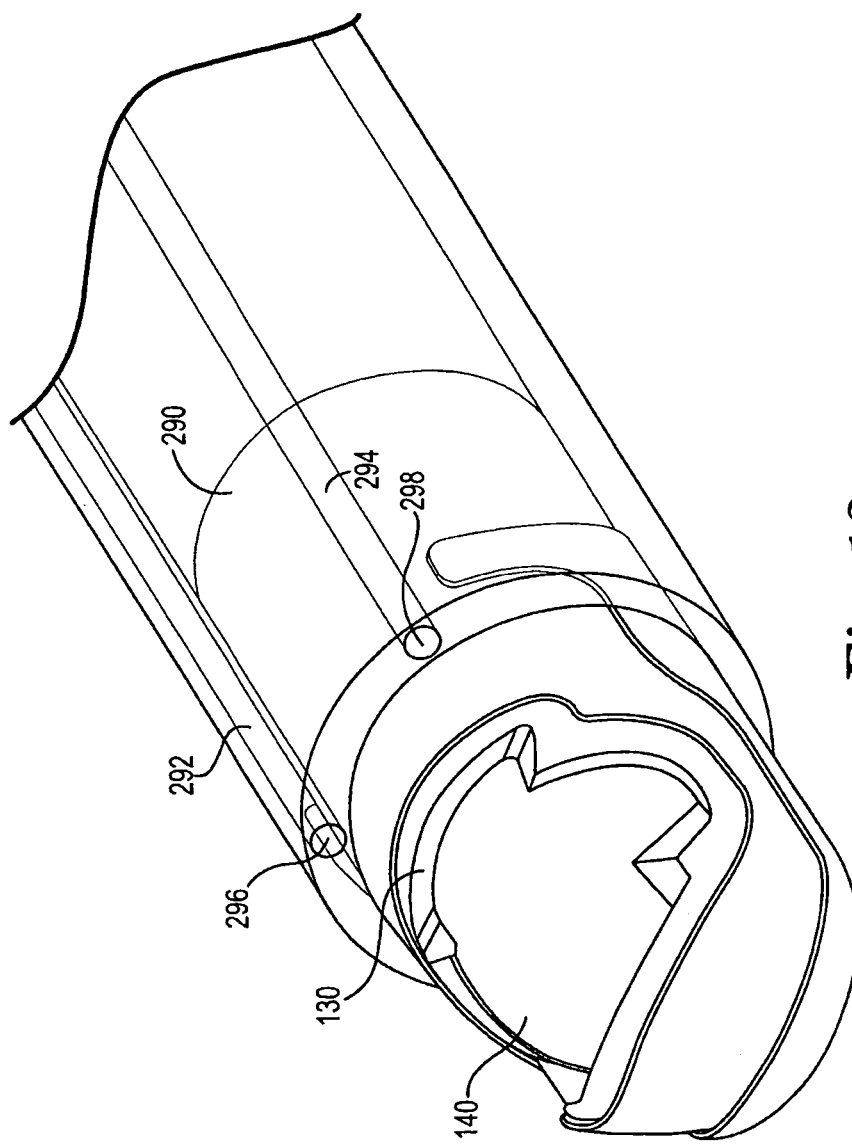
FIG. 12 is a perspective view of an example distal end region of an electrosurgical cutting device with irrigation channels formed within a molded sleeve surrounding an outer shaft.

In yet a further embodiment of fluid delivery illustrated in FIG. 12, a molded sleeve 290 is positioned over the outer shaft 130. The sleeve includes first and second irrigation channels 292 and 294 formed therein and spaced apart from one another to deliver fluid to first and second distribution points 296 and 298, respectively. Each of the first and second irrigation channels 292 and 294 is fluidly coupled with the fluid source 152 (FIGS. 1 and 5).

Figure 13:
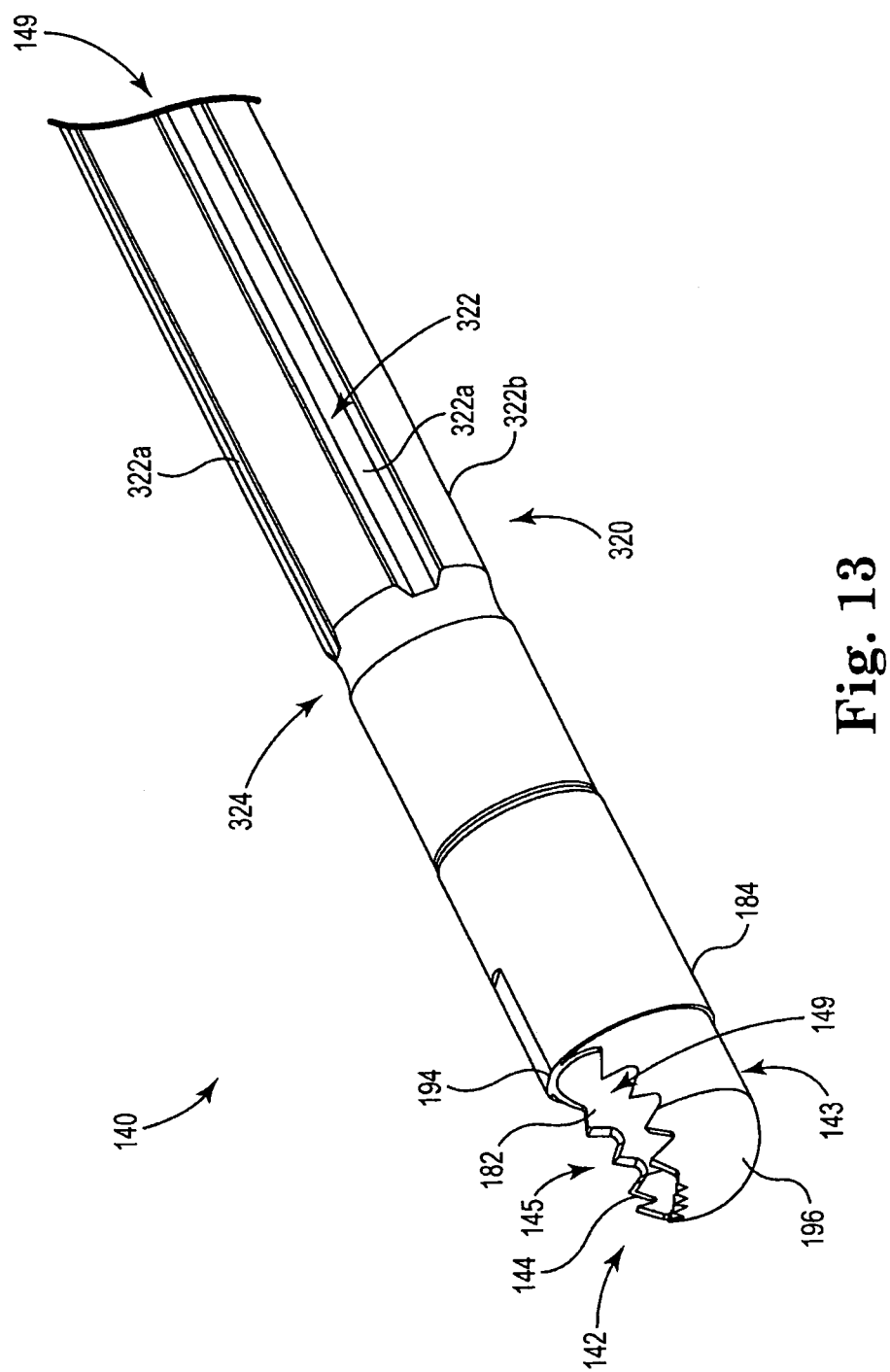
FIG. 13 is a perspective view of an example inner shaft of an electrosurgical cutting device having features for fluid delivery.

FIG. 13 shows another schematic example of fluid delivery. The inner shaft 140 of the example includes an insulated elongated portion 320 and an exposed and not coated inner cutter 143. The elongated portion 320 includes at least one fluid distribution flute 322 formed in the outer surface 184 of the inner shaft 140. The example shows a plurality of fluid distribution flutes 322a, 322b, . . . 322n formed into the inner shaft 140 and spaced-apart from each other around the circumference of the outer surface 184. At least one reservoir 324 is formed into outer surface 184 the inner shaft 140 and connected to the fluid distribution flutes 322a, 322b, . . . 322n as illustrated. In the example, reservoir 324 extends along the circumference of the outer surface 184.

Fluid collected from the reservoir can be dispersed from distribution points 161 and 162 on the outer shaft 130. When the inner shaft 140 is disposed within outer shaft 130, the inner surface 186 of outer shaft 130 combine with distribution flutes 322a, 322b, . . . 322n and reservoir to form lumen 137 described above with respect to FIGS. 2 and 3. In another example, detents can be formed in the inner surface 186 of outer shaft 130 in addition to or instead of distribution flutes 322 and reservoir 324 to form lumen 137. If detents are formed into the inner surface 186 of outer shaft 130, the outer surface 184 of inner shaft 140 can optionally be made smooth.

Figure 14:
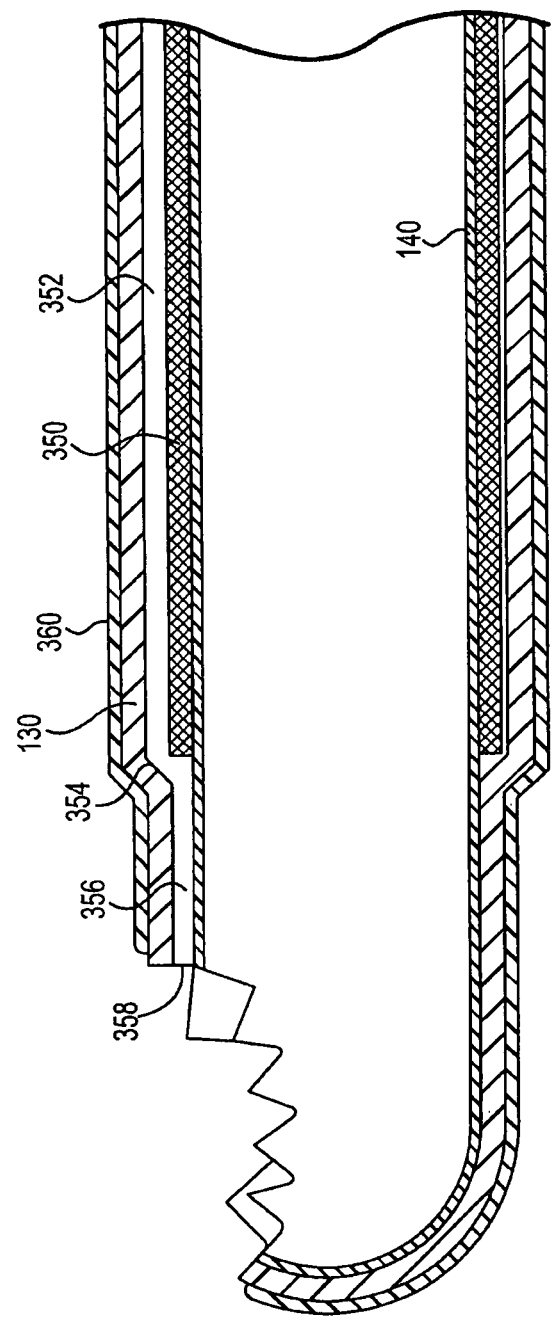
FIG. 14 is a side sectional view of a distal end region of an electrosurgical cutting device including an irrigation channel formed between an outer tube and an intermediate tube.

In another embodiment of fluid delivery illustrated in FIG. 14, an intermediate or middle tube 350 is positioned between the outer shaft 130 and the inner shaft 140. An irrigation channel 352 is formed between the intermediate tube and the outer tube and fluidly coupled to the fluid source 152 (FIGS. 1 and 5). The outer tube can include a shoulder 354 that directs fluid from the irrigation channel 352 to a distribution channel 356. Ultimately, fluid exits via a distribution point 358 positioned between the outer tube and the inner tube. In the specific embodiment illustrated, an outer insulation layer 360 is provided over the outer shaft 130, with a corresponding electrode (not shown) positioned on an exterior of the insulation layer 360.

Various modifications and alterations to this disclosure will become apparent to those skilled in the art without departing from the scope and spirit of this disclosure. It should be understood that this disclosure is not intended to be unduly limited by the illustrative embodiments and examples set forth herein and that such examples and embodiments are presented by way of example only with the scope of the disclosure intended to be limited only by the claims set forth herein as follows.

What is claimed is:
1. An electrosurgical device, comprising:
  a tubular outer shaft having an axis and a distal end region, wherein the distal end region includes a distal-most tip and a cutting edge defining an outer shaft window proximal along the axis to the distal-most tip;
  a tubular inner shaft coaxially maintained within the outer shaft such that the inner shaft is movable about the axis with respect to the outer shaft and wherein the inner shaft includes an outer surface having a toothed edge defining an opening, wherein the opening exposes an inner surface of the inner shaft in the window of the outer shaft when the opening is aligned with the window;
  a first electrode disposed on the outer shaft in a region proximal along the axis to the window;
  a fluid distribution point disposed on the outer shaft in a region proximal along the axis to the first electrode, the fluid distribution point configured to emit fluid across the first electrode and toward the distal-most tip; and
  a second electrode electrically isolated from the first electrode disposed on the inner shaft and exposed in the window of the outer shaft the second electrode including a first portion disposed on the outer surface of the inner shaft and a second portion disposed on the inner surface of the inner shaft;
  wherein a point on a surface of the first electrode is both axially aligned with the fluid distribution point and is located distally to the fluid distribution point along a line parallel with the axis;
  and further wherein an entirety of the first electrode is distal the fluid distribution point.

2. The electrosurgical device of claim 1 wherein the inner surface of the inner shaft forms a lumen configured to be in fluid communication with a suction source.

3. The electrosurgical device of claim 1 wherein the outer surface of the inner shaft and an inner surface of the outer shaft form a lumen in fluid communication with the fluid distribution point.

4. The electrosurgical device of claim 3 wherein the lumen includes an axial distribution flute and a reservoir in the distal end region.

5. The electrosurgical device of claim 4 wherein the axial distribution flute and reservoir are formed into the outer surface of the inner shaft.

6. The electrosurgical device of claim 1 wherein the first electrode is in electrical communication with an electrode surface on the outer surface of the outer shaft distal to the first electrode and electrically isolated from the cutting edge.

7. The electrosurgical device of claim 1 wherein the inner shaft and outer shaft are formed from a conductive material and are directly coated with an electrically insulating material, wherein the first and second electrodes are exposed and uncoated regions of the outer and inner shafts.

8. The electrosurgical device of claim 1, further comprising:
  a conductive ink trace positioned on the outer shaft;
  wherein the first electrode is electrically connected to the conductive ink trace and positioned on the outer shaft such that insulating material is positioned between the inner shaft and the first electrode.

9. The electrosurgical device of claim 8, wherein the insulating material comprises a coating positioned on the outer shaft.

10. The electrosurgical device of claim 8, wherein the outer shaft is formed of the insulating material.

11. The electrosurgical device of claim 8, wherein the conductive ink trace comprises silver ink.

12. The electrosurgical device of claim 8, wherein each of the first electrode and the inner shaft are selectively coupleable to an energy source.

13. The electrosurgical device of claim 8, wherein the outer shaft and inner shaft are configured to move relative to one another to mechanically cut tissue in a cutting mode.

14. The electrosurgical device of claim 8, wherein a lumen of the outer shaft is configured to allow fluid flow between the inner shaft and the outer shaft.

15. The electrosurgical device of claim 8, further comprising a button activation assembly comprising an electrical contact for providing electrical communication of the first electrode and inner shaft with a source of energy.

16. The electrosurgical device of claim 1, wherein the first electrode terminates at a distal-most end, and further wherein a section of the distal-most end is axially aligned with and distal to the fluid distribution point along the line parallel to the axis.

17. The electrosurgical device of claim 1, wherein an entirety of the first electrode is between the fluid distribution point and the window.

18. An electrosurgical device, comprising:
a tubular outer shaft having an axis and a distal end region, wherein the distal end region includes a distal-most tip and a cutting edge defining an outer shaft window proximal along the axis to the distal-most tip;
a tubular inner shaft coaxially maintained within the outer shaft such that the inner shaft is movable about the axis with respect to the outer shaft and wherein the inner shaft includes an outer surface having a toothed edge defining an opening, wherein the opening exposes an inner surface of the inner shaft in the window of the outer shaft when the opening is aligned with the window;
a first electrode disposed on the outer shaft in a region proximal along the axis to the window;
a fluid distribution point disposed on the outer shaft in a region proximal along the axis to the first electrode, the fluid distribution point configured to emit fluid across the first electrode and toward the distal-most tip; and
a second electrode electrically isolated from the first electrode disposed on the inner shaft and exposed in the window of the outer shaft the second electrode including a first portion disposed on the outer surface of the inner shaft and a second portion disposed on the inner surface of the inner shaft;
wherein a point on a surface of the first electrode is both axially aligned with the fluid distribution point and is located distally to the fluid distribution point along a line parallel with the axis;
and further wherein the inner shaft and outer shaft are formed from a conductive material and are directly coated with an electrically insulating material, wherein the first and second electrodes are exposed and uncoated regions of the outer and inner shafts.

19. An electrosurgical device, comprising:
a tubular outer shaft having an axis and a distal end region, wherein the distal end region includes a distal-most tip and a cutting edge defining an outer shaft window proximal along the axis to the distal-most tip;
a tubular inner shaft coaxially maintained within the outer shaft such that the inner shaft is movable about the axis with respect to the outer shaft and wherein the inner shaft includes an outer surface having a toothed edge defining an opening, wherein the opening exposes an inner surface of the inner shaft in the window of the outer shaft when the opening is aligned with the window;
a first electrode disposed on the outer shaft in a region proximal along the axis to the window;
a fluid distribution point disposed on the outer shaft in a region proximal along the axis to the first electrode, the fluid distribution point configured to emit fluid across the first electrode and toward the distal-most tip; and
a second electrode electrically isolated from the first electrode disposed on the inner shaft and exposed in the window of the outer shaft the second electrode including a first portion disposed on the outer surface of the inner shaft and a second portion disposed on the inner surface of the inner shaft;
wherein a point on a surface of the first electrode is both axially aligned with the fluid distribution point and is located distally to the fluid distribution point along a line parallel with the axis;
and further wherein an entirety of the first electrode is between the fluid distribution point and the window.

* * * * *